United States Patent
Horacek et al.

(10) Patent No.: US 7,884,122 B2
(45) Date of Patent: *Feb. 8, 2011

(54) EXTENDED RELEASE FORMULATION AND METHOD OF TREATING ADRENERGIC DYSREGULATION

(75) Inventors: Henry Joseph Horacek, Charlotte, NC (US); Min Michael He, Ellicott City, MD (US); Moise A. Khayrallah, Morrisville, NC (US)

(73) Assignee: Shionogi Pharma, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/615,477

(22) Filed: Nov. 10, 2009

(65) Prior Publication Data

US 2010/0063123 A1  Mar. 11, 2010

Related U.S. Application Data

(63) Continuation of application No. 12/134,444, filed on Jun. 6, 2008.

(60) Provisional application No. 60/942,934, filed on Jun. 8, 2007.

(51) Int. Cl.
- A01N 43/50 (2006.01)
- A61K 31/415 (2006.01)
- A61K 9/22 (2006.01)
- A61K 9/14 (2006.01)

(52) U.S. Cl. .................. 514/401; 424/468; 424/488

(58) Field of Classification Search .................. None
See application file for complete search history.

(56) References Cited

U.S. PATENT DOCUMENTS

| | | |
|---|---|---|
| 3,065,143 A | 11/1962 | Christenson et al. |
| 3,427,378 A | 2/1969 | Henderson et al. |
| 3,454,701 A | 7/1969 | Zeile et al. |
| 3,590,117 A | 6/1971 | Christenson et al. |
| 3,870,790 A | 3/1975 | Lowey et al. |
| 4,094,964 A | 6/1978 | Jarrott et al. |
| 4,140,755 A | 2/1979 | Sheth et al. |
| 4,167,558 A | 9/1979 | Sheth et al. |
| 4,201,211 A | 5/1980 | Chandrasekaran et al. |
| 4,226,849 A | 10/1980 | Schor |
| 4,259,314 A | 3/1981 | Lowey |
| 4,279,928 A | 7/1981 | Riley et al. |
| 4,292,303 A | 9/1981 | Keith et al. |
| 4,312,878 A | 1/1982 | Redmond, Jr. |
| 4,312,879 A | 1/1982 | Lal |
| 4,357,469 A | 11/1982 | Schor |
| 4,369,172 A | 1/1983 | Schor et al. |
| 4,389,393 A | 6/1983 | Schor et al. |
| 4,505,890 A | 3/1985 | Jain et al. |
| 4,540,566 A | 9/1985 | Davis et al. |
| 4,556,678 A | 12/1985 | Hsiao |
| 4,571,333 A | 2/1986 | Hsiao et al. |
| 4,578,264 A | 3/1986 | Stricker et al. |
| 4,587,257 A | 5/1986 | DeSantis et al. |
| 4,603,141 A * | 7/1986 | Giles .................. 514/385 |
| 4,612,008 A | 9/1986 | Wong et al. |
| 4,680,186 A | 7/1987 | Sheehy et al. |
| 4,685,918 A | 8/1987 | Amidon et al. |
| 4,734,285 A | 3/1988 | Alderman |
| 4,785,014 A | 11/1988 | Goldman-Rakic et al. |
| 4,795,327 A | 1/1989 | Gaylord et al. |
| 4,798,725 A | 1/1989 | Patel |
| 4,803,079 A | 2/1989 | Hsiao et al. |
| 4,851,228 A | 7/1989 | Zentner et al. |
| 4,871,548 A | 10/1989 | Edgren et al. |
| 4,874,613 A | 10/1989 | Hsiao |
| 4,880,632 A | 11/1989 | Lipham et al. |
| 4,883,649 A | 11/1989 | Counsell et al. |
| 4,894,240 A | 1/1990 | Geoghegan et al. |
| 4,902,515 A | 2/1990 | Loomis et al. |
| 4,931,281 A | 6/1990 | Kim et al. |
| 4,946,848 A | 8/1990 | Tuttle et al. |

(Continued)

FOREIGN PATENT DOCUMENTS

EP     0109320 B1     5/1984

(Continued)

OTHER PUBLICATIONS

ScienceLab.com. "Material Safety Data Sheet: Clonidine HCl" (2008). [Retrieved on Apr. 16, 2010]. Retrieved from the Internet: <URL:http://www.sciencelab.com/xMSDS-Clonidine_HCI-9923511>.*

Carter JC. "The Role of Lubricants in Solid Oral Dosage Manufacturing" (2006). [Retrieved on Apr. 16, 2010]. Retrieved from the Internet: <URL:http://www.carterpharmaceuticalconsulting.com/articles/role-of-lubricants-in-solid-oral-dosage-manufacturing.html>.*

Fyhrquist, "Comparison of sustained-release and standard preparations of clonidine in essential hypertension," Int. J. Clin. Pharmacol. Therapy Toxicol. 21(12):634-36 (1983).

(Continued)

Primary Examiner—Leslie A Royds
(74) Attorney, Agent, or Firm—Myers Bigel Sibley & Sajovec P.A.

(57) ABSTRACT

A composition and method of treating adrenergic dysregulation by administering the composition is disclosed, wherein the composition comprises a a2-adrenergic receptor agonist; a pharmaceutically acceptable hydrophilic matrix and a release-retardant of a metal alkyl sulfate. In embodiments, the composition provides a sustained release of the agonist, wherein after administration of the composition no more than once about every 12 hours to a subject having a steady state plasma concentration of the a2-adrenergic receptor agonist, the agonist's plasma concentration peak-to-trough ratio is no greater than about 1.9.

10 Claims, 10 Drawing Sheets

U.S. PATENT DOCUMENTS

| | | | |
|---|---|---|---|
| 4,968,508 | A | 11/1990 | Oren et al. |
| 4,981,696 | A | 1/1991 | Loomis et al. |
| 4,994,260 | A | 2/1991 | Kallstrand et al. |
| 4,996,058 | A | 2/1991 | Sinnreich |
| 5,002,776 | A | 3/1991 | Geoghegan et al. |
| 5,051,262 | A | 9/1991 | Panoz et al. |
| 5,082,668 | A | 1/1992 | Wong et al. |
| 5,126,145 | A | 6/1992 | Evanstad et al. |
| 5,133,974 | A | 7/1992 | Paradissis et al. |
| 5,175,052 | A | 12/1992 | Tokuda et al. |
| 5,178,868 | A | 1/1993 | Malmqvist-Granlund et al. |
| 5,209,746 | A | 5/1993 | Balaban et al. |
| 5,212,162 | A | 5/1993 | Missel et al. |
| 5,212,196 | A | 5/1993 | House et al. |
| 5,213,808 | A | 5/1993 | Bar-Shalom et al. |
| 5,221,278 | A | 6/1993 | Linkwitz et al. |
| 5,230,896 | A | 7/1993 | Yeh et al. |
| 5,275,824 | A | 1/1994 | Carli et al. |
| 5,288,497 | A * | 2/1994 | Stanley et al. ............... 424/440 |
| 5,419,917 | A | 5/1995 | Chen et al. |
| 5,484,607 | A | 1/1996 | Horacek |
| 5,869,100 | A | 2/1999 | Horacek |
| 6,030,642 | A | 2/2000 | Horacek |
| 6,080,426 | A | 6/2000 | Amey et al. |
| 6,245,350 | B1 | 6/2001 | Amey et al. |
| 6,287,599 | B1 | 9/2001 | Burnside et al. |
| 6,372,255 | B1 | 4/2002 | Saslawski et al. |
| 6,500,459 | B1 | 12/2002 | Chhabra et al. |
| 6,667,060 | B1 | 12/2003 | Vandecruys et al. |
| 6,811,794 | B2 | 11/2004 | Burnside et al. |
| 2002/0044966 | A1 | 4/2002 | Bartholomaeus et al. |
| 2003/0124191 | A1 | 7/2003 | Besse et al. |
| 2003/0190356 | A1 | 10/2003 | Yang et al. |
| 2004/0062800 | A1 | 4/2004 | Burnside et al. |
| 2004/0170684 | A1 | 9/2004 | Baichwal et al. |
| 2005/0051922 | A1 | 3/2005 | Nangia et al. |
| 2007/0196481 | A1 | 8/2007 | Amidon et al. |
| 2007/0275074 | A1 | 11/2007 | Holm et al. |
| 2008/0152709 | A1 | 6/2008 | Bortz |
| 2009/0087490 | A1 | 4/2009 | Horacek et al. |
| 2009/0110728 | A1 | 4/2009 | Rastogi et al. |
| 2009/0208584 | A1 | 8/2009 | Yoshinari et al. |

FOREIGN PATENT DOCUMENTS

| | | |
|---|---|---|
| EP | 0111144 B1 | 6/1984 |
| EP | 0797424 B1 | 10/1997 |
| WO | WO 95/21607 | 8/1995 |
| WO | WO 96/22768 A1 | 8/1996 |
| WO | WO 99/39700 | 8/1999 |
| WO | WO 00/41681 A2 | 7/2000 |
| WO | WO 01/22791 A2 | 4/2001 |
| WO | WO 2004/050019 A2 | 6/2004 |
| WO | WO 2005/020993 | 3/2005 |
| WO | WO 2005/041939 A1 | 5/2005 |
| WO | WO 2008/090569 A1 | 7/2008 |
| ZA | 200204331 | 3/2003 |

OTHER PUBLICATIONS

Horacek, "Clonidine extended-release capsules as an alternative to oral tablets and transdermal patches," J. Child Adolescent Psychopharmacol. 4(3): 211-12 (1994).

Horacek, "Extended-release clonidine for sleep disorders," J. Am. Acad. Child Adolesc. Psychiatry 33(8):1210 (1994).

Harron et al., "Alinidine pharmacokinetics following acute and chronic dosing," Br. J. Clin. Pharmacol. 13(6):821-27 (1982).

Steger, "Treatment of hypertensive out-patients with a sustained-release dosage form of clonidine: a comparison with standard tablet therapy and long-term follow-up study," Curr. Med. Res. Opin. 6(10):670-76 (1980).

Vocci at al., "Reformulation and drop size of apraclonidine hydrochloride," Am. J. Ophthalmol. Feb 15, 113(2):154-160 (1992).

Arndts, "New Aspects of the Clinical Pharmacology of Clonidine," Chest 83:397-400 (1983).

Arndts et al., "New Aspects of the Pharmacokinetics and Pharmacodynamics of Clonidine in Man," Eur. J. Clin. Pharmacol. 24:21-30 (1983).

*Chemical Abstracts, vol. 106, No. 26, Jun. 29, 1987, Columbus, Ohio US; abstract No. 219476; A.I. Tentsova et al.: "Mechanism of Clofelin Release From Solid Dispersion Systems With Ethyl Cellulose," Farmatsiya, vol. 36, No. 2, 1987 Moscow, pp. 16-19.

*Database WPI, Week 8714, Derwent Publications Ltd., London, GB; AN 87-099083 [14] JP 62 048 618 A (Zeria Shinyaku Kogyo KK) Mar. 3, 1987 (abstract).

*Database WPI, Derwent Publications Ltd., London, GB; AN 1987-218320 [31] JP 62 145014 A (Teijin Ltd.), Jun. 29, 1987 (abstract).

Davies et al., Pharmacokinetics and concentration-effect relationships of intraveneous and oral clonidine Clin. Pharmacol. Ther. 21:593-601 (1977).

Dollery et al., "Clinical pharmacology and pharmacokinetics of clonidine," Clin. Pharmacol. Ther. 19:11-17 (1975).

English translation of STEGER, "On the ambulant treatment of hypersensitive patients with Catapresan® Depot Perlongets Comparison of the action of Catapresan® tablets and long-term trial," Therapiewoche 29:5202-06 (1979).

Frisk-Holmberg et al., "Clonidine kinetics in man-evidence for dose dependency and changed pharmacokinetics during chronic therapy," Br. J. Clin. Pharmacol. 12:653-58 (1981).

Fujimura et al., "Comparison of the Pharmacokinetics, Pharmacodynamics, and Safety of Oral (Catapres) and Transdermal (M-5041T) Clonidine in Healthy Subjects," J. Clin. Pharmacol. 34:260-265 (1994).

Garrett et al., "Clonidine in the Treatment of Hypertension," J. Cardiovasc. Pharmacol. 2:S61-S71 (1980).

Hashimoto et al., Therapeutic effects of evening administration of guanabenz and clonidine on morning hypertension: evaluation using home-based blood pressure measurements, J. Hypertens. 21:805-11 (2003).

Hunt et al., "Clonidine in Child and Adolescent Psychiatry," J. Child Adolescent Psychopharmacol. 1:87-102 (1990).

International Search Report and Written Opinion, PCT/US2008/066036, mailed Jul. 30, 2009.

Jain et al., "Efficacy and acceptability of different dosage schedules of clonidine," Clin. Pharmacol. Ther. 21:382-87 (1977).

Kanto et al., "Bioavailability and clinical effects of three brands of clonidine: the relationship between plasma level and effect," Int. J. Clin. Pharmacol. Ther. Toxicol. 20:118-21 (1982).

Keränen et al., "Pharmacokinetics and Side-Effects of Clonidine," Eur. J. Clin. Pharmacol. 13:97-101 (1978).

Lawson et al., "Clonidine in hypertension: a 6-year review," Curr. Med. Res. Opin 6:168-174 (1979).

Lehtonen, "Clonidine Depot Form in Hypertension," Curr. Ther. Res. 24:831-37 (1978).

Levina et al., abstract, "The Influence of Starch® on Drug Release from HPMC Matrices," Am. Assoc. Pharm. Sci. Annu. Meeting, Oct. 2001.

Lowenthal, "Pharmacokinetics of Clonidine," J. Cardiovasc. Pharmacol. 2:S29-S37 (1980).

Lowenthal et al., "Efficacy of clonidine as transdermal therapeutic system: The international clinical trial experience," Am. Heart J. 112:893-900 (1986).

MacGregor et al., "Pharmacokinetics of oral sustained release clonidine in humans," Arzneimittelforschung 35:440-46 (1985).

Mancia et al., "Evaluation of a Slow-Release Clonidine Preparation by Direct Continuous Blood Pressure Recording in Essential Hypertensive Patients," J. Cardiovasc. Pharmacol. 3:1193-1202 (1981).

Onesti et al., "Clonidine: A New Antihypertensive Agent," Am. J. Cardiol. 28:74-83 (1971).

Parati et al., Abstract No. 140, "An Evaluation of the Antihypertensive Effect of Slow Release Clonidine by Direct and Continuous Blood Pressure Recording in Ambulant Hypertensive Subjects," Eur. J. Clin. Invest. 11:24 (1981).

Popli et al., "Transdermal Clonidine in Mild Hypertension," Arch. Intern. Med. 146:2140-44 (1986).

Rodrigues et al., "Comparison of sustained-release clonidine and long-acting propranolol in the treatment of hypertension," Curr. Med. Res. Opin. 8:274-81 (1982).

Shaffer et al., "A comparison of standard and sustained release clonidine with respect to plasma concentration and blood pressures changes," Br. J. Clin. Pharmacol. 19:524-26 (1985).

Steger, "Zur ambulanten Behandlung von Hypertonikern mit Catapresan® Depot Perlongetten," Therapiewoche 29:5202-06 (1979).

Weber et al., "Transdermal Administration of Clonidine for Treatment of High BP," Arch. Intern. Med. 144:1211-13 (1984).

Wilkinson et al., "A Comparative Trial of Clonidine, Propranolol and Placebo in the Treatment of Moderate Hypertension," Br. J. Clin. Pharmacol. 4:289-94 (1977).

Wing et al., Pharmacokinetic and concentration-effect relationships of clonidine in essential hypertension, Eur. J. Clin. Pharmacol. 12:463-69 (1977).

Yeh et al., "Antihypertensive Effect of Clonidine Its Use Alone and in Combination With Hydrochlorothiazide and Guanethidine in the Treatment of Hypertension,"Arch. Intern. Med. 127:233-37 (1971).

U.S. Appl. No. 12/560,648, filed Sep. 16, 2009.

U.S. Appl. No. 12/645,772, filed Dec. 23, 2009.

* cited by examiner

EXTENDED RELEASE FORMULATION AND METHOD OF TREATING ADRENERGIC DYSREGULATION

This application is a continuation application of, and claims priority to, U.S. application Ser. No. 12/134,444, filed Jun. 6, 2008, which claims the benefit of U.S. Provisional Application No. 60/942,934, filed Jun. 8, 2007. The entire contents of each of these applications is incorporated by reference herein.

FIELD OF THE INVENTION

Compositions and methods of treatment and prevention of adrenergic dysregulation are disclosed.

BACKGROUND OF THE INVENTION

Adrenergic dysregulation (hyperadrenergia or hypoadrenergia) refers to abnormal neuronal activation or secretion of the hormone adrenaline and/or the neurotransmitter noradrenaline. Adrenergic dysregulation may occur at both baseline levels of stimulation and in response to external stress. Excessive adrenergic stimulation results in symptoms such as high blood pressure, hyperactivity, physical aggression, motor tics, and insomnia.

Effective drug therapies require control of blood serum levels of drug. Time release hydrophilic matrices are known in the field of drug formulations. For example, one such hydrophilic matrix is hydroxypropyl methylcellulose (HPMC). HPMC matrixes in a surrounding medium of low ionic strength with electrolytes typically hydrate to produce an intact gel layer. An intact gel layer may provide predictable release of an incorporated drug from the matrix by migration through the gel layer. However, at intermediate ionic strengths, the same matrix may lose shape and disintegrate rapidly. Thus, electrolytes present in the surrounding medium may modify the release profile of drugs from HPMC matrices. Modification of the release profile of a drug resulting from differences in matrix environment may be detrimental to the therapeutic usefulness of a drug.

Drugs themselves may also influence the rate of hydration and the rate of gelation of hydrophilic matrixes. (Mitchell, et al., *Int. J. Pharm.* (1993) 100: 165-173). Therefore, the incorporation of drugs in hydrophilic matrices may result in unpredictable dissolution profiles, which may result in unpredictable therapeutic efficiency of the dosage forms.

Drug release from an oral solid extended release dosage form and subsequent absorption of the drug from the gastrointestinal tract into the blood stream is dissolution-rate dependent and may be slow and irregular especially in the case of sparingly water soluble, slightly water soluble, very slightly water soluble, practically water insoluble, or a water insoluble drug, as defined according to the United States Pharmacopeia 24, p 10.

Additives may be added to hydrophilic matrixes to modify the gelling rate and/or the release rate of an incorporated drug. However, the nature of the interaction of a particular drug with the matrix and additive is not generally predictable. This is particularly problematic for drugs administered in low dosages or drugs with limited solubility. It is also difficult to correlate the release rate of a drug with its serum or blood concentration when complex matrix/additive systems are used.

The traditional oral dosage formulations of $\alpha_2$-adrenergic receptor agonists have disadvantages. The release profile of the traditional oral dose is typically a rapid and bolus release followed by rapid and complete absorption. For example, the traditional oral formulation of clonidine has side-effects including sedation about an hour after the given dose, when the patient may become transiently sedated or fall asleep. Because of the rapid absorption of the drug, the half-life of this dosage form of clonidine is essentially the same as the biological half-life of about four to six hours. Thus, in the traditional formulation of clonidine, the therapeutic effect may wear off too soon and possibly be accompanied with rebound hyperarousal. This may occur in the middle of the night causing insomnia and nightmares. Such side effects have limited the practical usefulness of orally administered clonidine. Despite the usefulness of clonidine in the treatment of hypertension, the regimen of administration required by the pharmacokinetic profile of the drug resulted in quite wide fluctuations in plasma concentrations, even at steady state. (Fujimura A., et al., *J. Clin. Pharmacol.* 1994; 34:260-265). It has been shown that many of the adverse events (AEs) observed during oral clonidine administration were related to its high peak plasma concentrations. (Lowenthal D T., *J. Cardiovasc. Pharmacol.*, 1980; 2(suppl.):S29-S37).

The pharmacokinetic profile and relationship between plasma levels and AEs necessitate frequent dosing and result in a "roller coaster" effect characterized by "peak" AE of sedation and trough AE of rebound hypertension. In an effort to address the "roller coaster" issue, a 7-day patch formulation for clonidine (marketed under the brand name Catapres-TTS) was developed. Early studies showed that transdermal administration of clonidine was safe and effective in controlling hypertension (Weber, M A, et al., *Arch. Intern. Med.*, 1984; 144(6):1211-1213. In addition, these studies suggested a milder AE profile for the patch formulation than for oral clonidine with reduced sedation and lack of rebound hypertension. The patch, however, had severe limitations. First, localized skin reactions such as erythema, pruritus and localized vesiculation was observed in over 50% of patients. In a large database of exposure to transdermal clonidine reviewed by the FDA, these skin reactions led to discontinuation of treatment in 19% of patients. Furthermore, the label cautions that in patients who develop an allergic reaction to transdermal clonidine, substitution of oral clonidine may also elicit an allergic reaction including generalized rash, urticaria or angioedema. Another problem that has plagued the patch is poor adhesiveness necessitating the use of an adhesive overlay.

A capsule containing microcapsule having a range of differing release profiles has been used as a sustained release formulation of clonidine. (Mancia, G. et al., *J. Cardiovasc. Pharmacol.*, 1981; 3:1193-1202; Fyhrquist, F., *Intl. J. Clin. Pharmacol., Therapy and Toxicol.*, 1983; 21:12:634-636). This formulation is known as Catapresan-Perlonget and is available in Europe. Typically, the sustained release formulation contains different membrane coated nuclei of the drug. One nuclei releases the drug rapidly while the others release more slowly over 3 or 6 hours, respectively. (Mancia).

For the foregoing reasons, there is a need for drug formulations, such as low dosage drug formulations, that are capable of stable therapeutic dosage profiles by providing an extended serum level concentration of active for an extended period in order to avoid possible "peak and trough" side effects (effectiveness at peak serum levels and rebound exacerbation of symptoms at trough levels).

SUMMARY

Figure 1A:
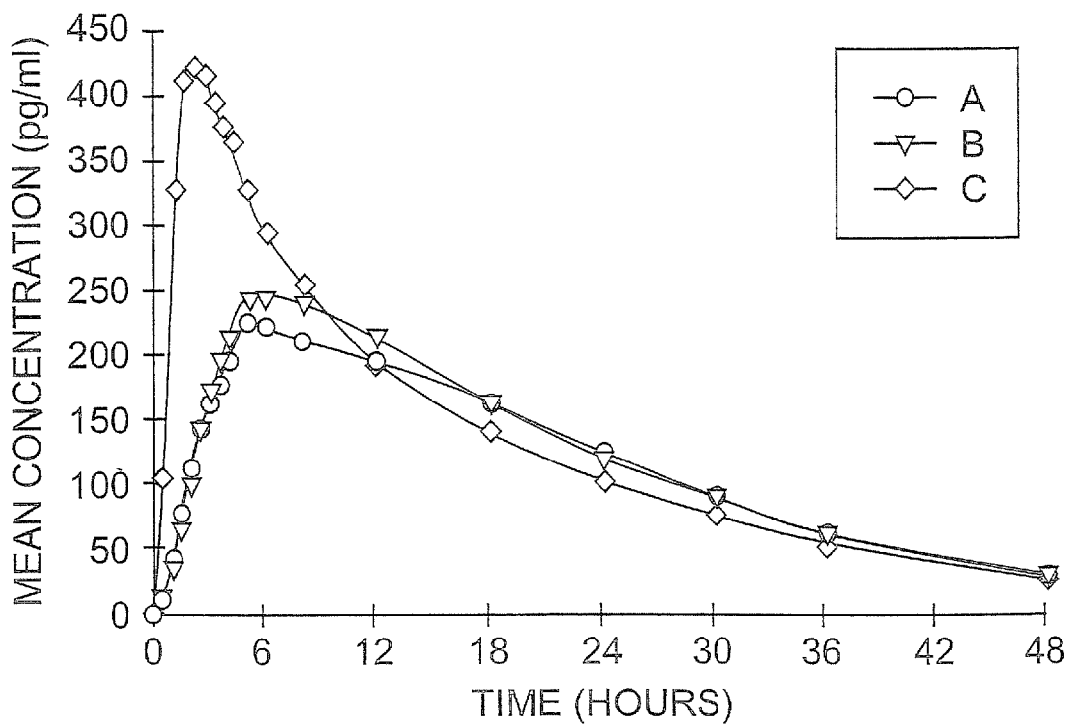
FIGS. 1A and 1B depict the mean Clonidine concentration-time profiles after administration of Clonicel-Fasted (Treatment A), Clonicel-Fed (Treatment B) and Catapres-Fasted (Treatment C).

Described herein is an oral dosage form comprising: (a) an $\alpha_2$-adrenergic receptor agonist in an amount between 0.001 wt % and 0.5 wt % of said oral dosage form; and (b) a pharmaceutically acceptable hydrophilic matrix comprising: (i) at least one hydroxypropyl methylcellulose ether in an amount between 20 wt % and 80 wt % of the oral dosage form; (ii) at least one of starch, lactose, or dextrose in an amount between 20 wt % and 80 wt % of the oral dosage form; and (iii) a metal alkyl sulfate; wherein after administration of the oral dosage form no more than once about every 12 hours to a subject having a steady state plasma concentration of the $\alpha_2$-adrenergic receptor agonist, the agonist's plasma concentration peak-to-trough ratio is no greater than about 1.9.

In another embodiment, a method of treating adrenergic dysregulation in a subject in need thereof is disclosed. The method comprises, orally administering to the subject no more than once about every 12 hours the oral dosage formulation described herein, which provides a plasma peak-to-trough ratio no greater than about 1.9, wherein the adrenergic dysregulation is treated.

DETAILED DESCRIPTION

In one embodiment, an oral dosage form is provided. The dosage form comprises an $\alpha_2$-adrenergic receptor agonist in an amount between 0.001 wt % and 0.5 wt % of the oral dosage form; a pharmaceutically acceptable hydrophilic matrix comprising a mixture of at least one hydroxypropyl methylcellulose ether in an amount between 20 wt % and 80 wt % of the oral dosage form; at least one of starch, lactose, or dextrose in an amount between 80 wt % and 20 wt % of the oral dosage form; a release-retardant of a metal alkyl sulfate; and optionally a metal stearate and/or colloidal silica.

In another embodiment, an oral dosage form is disclosed, wherein the oral dosage form comprises: (a) an $\alpha_2$-adrenergic receptor agonist in an amount between 0.001 wt % and 0.5 wt % of said oral dosage form; and (b) a pharmaceutically acceptable hydrophilic matrix comprising: (i) at least one hydroxypropyl methylcellulose ether in an amount between 20 wt % and 80 wt % of the oral dosage form; (ii) at least one of starch, lactose, or dextrose in an amount between 20 wt % and 80 wt % of the oral dosage form; and (iii) a metal alkyl sulfate; wherein after administration of the oral dosage form no more than once about every 12 hours to a subject having a steady state plasma concentration of the $\alpha_2$-adrenergic receptor agonist, the agonist's plasma concentration peak-to-trough ratio is no greater than about 1.9.

In another embodiment, disclosed is an oral dosage form comprising: (a) an $\alpha_2$-adrenergic receptor agonist in an amount between 0.001 wt % and 0.5 wt % of the oral dosage form; and (b) a pharmaceutically acceptable hydrophilic matrix comprising: (i) at least one hydroxypropyl methylcellulose ether in an amount between 20 wt % and 80 wt of said oral dosage form; (ii) at least one of starch, lactose, or dextrose in an amount between 20 wt % and 80 wt % of the oral dosage form; and (iii) a metal alkyl sulfate; wherein after a first administration to a subject of the dosage form, the agonist's plasma concentration peak-to-trough ratio is no greater than about 1.9 for any subsequent administration of the dosage form, wherein the subsequent administration is no more than once about every 12 hours.

In yet another embodiment, a solid oral dosage form for treating and/or reducing an adrenergic dysregulation condition in a subject in need thereof is disclosed. The solid oral dosage form comprises, a) an $\alpha_2$-adrenergic receptor agonist; b) a pharmaceutically acceptable hydrophilic matrix providing a release rate of the $\alpha_2$-adrenergic receptor agonist; and c) a release-retardant in an amount such that the release rate of the $\alpha_2$-adrenergic receptor agonist from the hydrophilic matrix is decreased.

In another embodiment, a method of treating an adrenergic dysregulation condition in a subject in need thereof is disclosed. The method comprises, orally administering to a subject a formulation comprising an effective amount of an $\alpha_2$-adrenergic receptor agonist, the $\alpha_2$-adrenergic receptor agonist admixed within a pharmaceutically acceptable hydrophilic matrix comprising a release-retardant; and providing an extended release rate of the $\alpha_2$-adrenergic receptor agonist from the formulation; wherein the extended release rate of the $\alpha_2$-adrenergic receptor agonist from the pharmaceutically acceptable hydrophilic matrix with the release-retardant admixed therein is less than a release rate for the $\alpha_2$-adrenergic receptor agonist from the pharmaceutically acceptable hydrophilic matrix without the release-retardant admixed therein. In this embodiment, the method can further include, providing (i) a plasma concentration level of the $\alpha_2$-adrenergic receptor agonist from the pharmaceutically acceptable hydrophilic matrix; and (ii) a peak plasma level concentration of the α₂-adrenergic receptor agonist from the pharmaceutically acceptable hydrophilic matrix; wherein the plasma concentration level of α₂-adrenergic receptor agonist from the pharmaceutically acceptable hydrophilic matrix with the release-retardant admixed therein provides an extended plasma concentration level of the α₂-adrenergic receptor agonist and a reduced peak plasma level concentration of the α₂-adrenergic receptor agonist than a pharmaceutically acceptable hydrophilic matrix and the α₂-adrenergic receptor agonist without the release-retardant admixed therein. In this embodiment, the extended release rate of the α₂-adrenergic receptor agonist from the pharmaceutically acceptable hydrophilic matrix is zero-order to first-order.

In another embodiment, a method of treating adrenergic dysregulation in a subject in need thereof is provided. The use of the present formulations may provide for improved therapies for symptoms manifesting from adrenergic dysregulation conditions by systemic control of catecholamines. The method comprises orally administering to the subject a formulation comprising an effective amount of an α₂-adrenergic receptor agonist the α₂-adrenergic receptor agonist admixed within a pharmaceutically acceptable hydrophilic matrix comprising a release-retardant. The method provides an extended release rate of the α₂-adrenergic receptor agonist. The extended release rate of the α₂-adrenergic receptor agonist from the pharmaceutically acceptable hydrophilic matrix with the release-retardant admixed therein is less than a release rate for the α₂-adrenergic receptor agonist from the pharmaceutically acceptable hydrophilic matrix without the release-retardant admixed therein.

In yet another embodiment, disclosed is a method of treating adrenergic dysregulation in a subject in need thereof, comprising: administering an oral dosage form as described herein to a subject no more than once about every 12 hours, wherein the subject has a steady state plasma concentration of the α₂-adrenergic receptor agonist, and wherein after the administering, the agonist's plasma concentration peak-to-trough ratio is no greater than about 1.9; wherein the adrenergic dysregulation is treated.

The α₂-adrenergic receptor agonist can be any compound or composition of matter that binds to the α₂-adrenergic receptor of a cell to produce a central α-adrenergic stimulation within the cell. Examples of α₂-adrenergic receptor agonists include epinephrine, noradrenaline, isoprenaline, clonidine, guanfacine, lofexidine, xylazine, or their salts. In preferred embodiments, the agonist is clonidine or a pharmaceutically acceptable salt thereof. Most preferably, the agonist is clonidine hydrochloride. The aforementioned agonists may be supplied as pure compounds, or in a form of a pharmaceutically active salt, isomer, a racemic mixture, or in any other chemical form or combination that, under physiological conditions, provides for therapeutically effective treatment of adrenergic dysregulation.

As used herein, "clonidine" refers to a 9-carbon, two-ringed imidazoline derivative. The term "clonidine" denotes generally one or more of 2,6-dichloro-N-2-imidazolidinylidene benzeneamine, or benzeneamines structurally and functionally related thereto that are described in U.S. Pat. No. 3,454,701. U.S. Pat. No. 3,454,701, is incorporated herein by reference for its disclosure of such structurally and functionally related benzeneamines. As used herein, lofexidine refers to 2-[1-(2,6-dichlorophenoxy)ethyl]-4,5-dihydro-1H-imidazole or structurally and functionally related imidazoles. As used herein, xylazine refers to 2-(2,6-dimethylphenylamino)-5,6-dihydro-4H-thiazine or structurally and functionally related thiazines. With respect to the preferred embodiments of the present invention, the term "clonidine" denotes 2,6-dichloro-N-2-imidazolidinylidene benzeneamine, and its various tautomers and rotomers. In a preferred embodiment, it has the following structure:

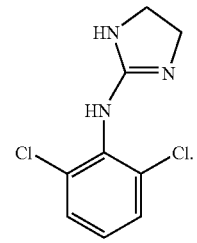

The amount of α₂-adrenergic receptor agonists that is included per oral dosage form may vary widely. For example, the therapeutically effective dose range for the α₂-adrenergic receptor agonist clonidine is about 0.025 mg to about 0.40 mg per dosage form for most of the symptoms of the clinical disorders listed above. The therapeutically effective dose range of about 0.025 mg to about 0.40 mg per dosage form typically controls most of the symptoms of adrenergic dysregulation.

Adrenergic dysregulation refers generally to conditions of cardiovascular, analgesic, neurologic/psychiatric, or gastrointestinal/renal origin resulting from abnormal neuronal activation or secretion of adrenaline and/or noradrenaline. By way of example, cardiovascular conditions include those conditions manifested in hypertension, atrial fibrillation, congestive heart failure, and orthostatic hypotension. Analgesic conditions include those conditions manifested in intraoperative and postoperative pain, intractable cancer pain, headaches, labor pain, and reflex sympathetic dystrophy. Neurologic/psychiatric conditions include those conditions manifested in akathisia, peripheral neuropathy, neuropathic orofacial pain, diabetic gastroparesis, essential tremor, postepidural shivering, postanesthesia shivering, restless legs syndrome, hypertonicity, hyperkinetic movement disorders, Tourette's syndrome, substance withdrawal, acute anorexia nervosa, attention-deficit/hyperactivity disorder (ADHD), conduct disorder, bipolar disorder, aggression, narcolepsy, panic disorder, posttraumatic stress disorder, sleep disorders, social phobia, and schizophrenia. Gastrointestinal/renal conditions include those conditions manifested in ulcerative colitis and proctitis, emesis, and cyclosporine-induced nephrotoxicity. Endocrine/hormonal conditions include those conditions manifested in hyperthyroidism, growth delay in children, excessive sweating, post-menopausal flushing, and hot flashes.

Attention Deficit Hyperactivity Disorder and ADHD refer to any etiological or pathological symptom associated with the disorder. Such symptoms and etiology include inattention, hyperactivity and impulsivity. Generally, a subject will exhibit significant impairment occurring in at least two settings and/or consistently display such characteristic behaviors over an extended period of time. The terms also include Attention Deficit Disorder (ADD).

Hypertension refers generally to any etiological or pathological symptom manifested in blood pressure that is chronically elevated. Such symptoms include low-renin levels, insulin resistance, sleep apnea, excess serum sodium levels, obesity and genetic disposition.

Useful amounts of agonist present in the formulation are between about 0.001 wt % and 0.5 wt % of the dosage form.

Preferably, the amount is between about 0.01 wt % and about 0.3 wt %. More preferably, the amount is between about 0.05 wt % and 0.2 wt %.

Useful amounts of the hydroxypropyl methylcellulose ether(s) are between about 20 wt % and 80 wt % of the dosage form. Preferably, the amount is between about 30 wt % and 50 wt %. More preferably, the amount is between about 40 wt % and 60 wt %. Most preferably, the amount is between about 20 wt % and 40 wt %, or 60 wt % and 80 wt %.

Useful amounts of starch, lactose or dextrose are between about 20 wt % and 80 wt % of the dosage form. Preferably, the amount is between about 50 wt % and 70 wt %. More preferably, the amount is between about 40 wt % and 60 wt %. Most preferably, the amount is between about 20 wt % and 40 wt %, or 60 wt % and 80 wt %.

Useful amounts of metal alkyl sulfate are between about 1 wt % and 8 wt % of the dosage form. Preferably, the amount is between about 1 wt % and 7 wt %. More preferably, the amount is between about 2 wt % and 6 wt %. Most preferably, the amount is about 2 wt %. Metal alkyl sulfates are known in the art and include, for example, ammonium lauryl sulfate, magnesium laureth sulfate, sodium dodecyl sulfate (sodium lauryl sulfate), sodium laureth sulfate, sodium myreth sulfate and sodium pareth sulfate. Preferably, the metal alkyl sulfate is sodium lauryl sulfate (SLS).

The useful and preferred values of the dosage form are also useful and preferred values when used in the methods described herein.

The peak-to-trough ratio is defined as the highest blood plasma concentration divided by the lowest blood plasma concentration within a dosing interval. The dosing interval is the time from the administration of a dose to the time of the next administration. Determining the time at which blood plasma can be measured to ensure the highest and lowest concentrations are determined is within the purview of a skilled artisan.

Minimizing the fluctuation in plasma concentration yields beneficial results. The leveling of the blood plasma concentrations over a dosing interval and, consequently, over the course of potentially long-term therapy provides the consistent plasma levels necessary to treat or ameliorate $\alpha_2$-adrenergic dysregulation. A useful peak-to-trough ratio is no greater than about 1.9. Preferably, the ratio is no greater than about 1.6. Also preferred is a ratio between about 1.1 and about 1.6. Most preferably, the ratio is between about 1.3 and 1.6. The most preferred ratio is about 1.4. The lower the ratio, the less fluctuation and, therefore, there are fewer associated side effects.

Steady-state is defined as the plasma concentration levels after about five half-lives. Thus, steady-state is reached at different times for different actives. Clonidine's half-life is about 12 to 17 hours. Therefore, clonidine steady-state is reached at about day four.

The hydrophilic matrix provides for a controlled pharmacokinetic release profile of the $\alpha_2$-adrenergic receptor agonist. The hydrophilic matrix provides for a zero- to first-order release profile of the $\alpha_2$-adrenergic receptor agonist. When using a combination of components for the hydrophilic matrix, the ratio of the components may influence the release profile of the $\alpha_2$-adrenergic receptor agonist from the matrix. For a low dose $\alpha_2$-adrenergic receptor agonist (for example, clonidine) the ratio of the components may not be predictable or determinable. By adjusting the amount of hydrophilic polymer and/or release-retardant compared to the $\alpha_2$-adrenergic receptor agonist, the release profile of the $\alpha_2$-adrenergic receptor agonist may be adjusted or more easily tailored to a particularly advantageous therapeutically effective profile.

By releasing the drug over a longer period of time, therapeutically effective profiles of up to and including 24 hour dosing of the $\alpha_2$-adrenergic receptor agonist is provided with reduction or elimination of undesirable side effects, such as hyperarousal. More specifically, the formulation disclosed herein provides minimal fluctuation of plasma concentrations of an $\alpha_2$-adrenergic receptor agonist, such as clonidine at steady-state.

The data provided herein show that the present formulation provides plasma concentrations at steady state that are predictable from day to day. Further, when measured on two days separated by 48 hours, the concentrations were very similar on a patient by patient basis indicating consistent performance between individual drug units. The narrow peak-to-trough plasma concentrations provide a therapeutically effective amount of active without the roller-coaster effect that comes with the high peak-to-trough fluctuations seen in prior art formulations. The present formulation provides blood levels achieved from the clonidine patch in an oral sustained-release tablet. In its review of data from the clonidine patch, FDA noted that the peak to trough ratio in steady state concentrations observed with the clonidine patch averaged about 1.33 whereas the corresponding fluctuation with the immediate release clonidine tablet averaged 2.10. Data from the present study show average ratios with Clonicel of about 1.4 to about 1.5, which are ratios that are much closer to the clonidine patch than to the immediate release tablet.

The term "hydrophilic matrix" refers to one or more natural or synthetic materials that are hydrophilic, but not necessarily water-soluble. Examples of a hydrophilic matrix include polymer or polymers having affinity for absorbing water such as cellulose ethers (e.g., hydroxypropyl methylcellulose), mono or disaccharides (for example, dextrose or lactose), starch, derivatives thereof, alone or in combination.

The term "starch" refers generally to a mixture of polysaccharides of plant origin, the polysaccharides including amylose and amylopectin. Starch includes, for example, sorghum, plantain and corn starches. The term "starch" includes material that has been chemically- and/or mechanically-processed in the presence of water and subsequently dried. By way of example, the term "starch" includes pregelatinized starch, which encompasses completely chemically- and/or mechanically-processed starch or mixtures of partially and completely chemically- and/or mechanically-processed starches. Partially pregelatinized starch includes, for example a mixture comprising one or more of a modified starch and one or more of an unmodified starch, each starch independently selected from sorghum, plantain and corn starches.

The term "lactose" refers to a chemical compound comprising a β-D-galactose and a β-D-glucose molecule linked through a $\beta_{1-4}$ glycosidic chemical bond, and derivatives thereof. Lactose may be provided in any form, e.g., spray dried, modified spray dried, or hydrated.

The term "dextrose" refers to a chemical compound comprising a glucose molecule and derivatives thereof. D-glucose is preferred. Dextrose may be provided in any form, e.g., spray dried, modified spray dried, or hydrated.

As used herein, the term "treatment" and its grammatical equivalents refer to the alleviation or elimination of etiological or pathological symptoms and include, for example, the elimination of such symptom causation either on a temporary or permanent basis, or to alter or slow the appearance of such symptoms or symptom worsening. For example, the term "treatment" includes alleviation or elimination of causation of symptoms associated with, but not limited to, adrenergic dysregulation or its related-complications described herein. Treatment includes the prevention of the associated condition.

"Therapeutically effective" refers qualitatively to the amount of an agent or agents in combination for use in adrenergic dysregulation therapy that is nontoxic but sufficient to provide the desired effect that will achieve the goal of preventing, or improvement in the severity of the symptoms. Adrenergic dysregulation or its related complication symptoms is considered prevented or improved if any benefit is achieved, irrespective of the absolute magnitude of the amelioration or improvement. For example, any reduction in blood pressure of a subject suffering from hypertension would be considered an ameliorated symptom. Likewise, any inhibition or suppression of inattention, hyperactivity and impulsivity would also be considered amelioration of ADHD. Furthermore, any reduction or elimination in side-effects such as "peak and trough" side effects of transient sedation at peak serum levels and rebound exacerbation of symptoms at trough levels of a subject on an ADHD therapy is considered an ameliorated symptom.

As used herein, "therapeutically effective amount" refers to an amount of an active agent. The therapeutically effective amount varies according to the patient's sex, age and weight, the route of administration, the nature of the condition and any treatments, which may be associated therewith, or any concurrent related or unrelated treatments or conditions of the patient. In determining the effective amount or dose, a number of factors are considered by the attending diagnostician, including, but not limited to, the potency and duration of action of the compounds used, the nature and severity of the illness to be treated, as well as the sex, age, weight, general health and individual responsiveness of the patient to be treated, and other relevant circumstances. Therapeutically effective amounts may be determined without undue experimentation by any person skilled in the art or by following the exemplary guidelines set forth in this application.

As used herein, the term "subject" for purposes of treatment or prevention includes any subject, and preferably is a subject who is in need of an adrenergic dysregulation treatment, or who needs treatment of an adrenergic dysregulation related complication. For purposes of prevention, the subject is any subject, and preferably is a subject that is at risk for, or is predisposed to, an adrenergic dysregulation condition or its related complications. The subject is typically an animal, more typically is a mammal. Preferably, the mammal is a human, horse, dog or cat.

As used herein, the terms "subject" in need thereof and grammatical equivalents refer to any subject who is suffering from or is predisposed to an adrenergic dysregulation condition or its related complications. The terms include any subject that requires a lower dose of therapeutic agents. In addition, the terms include any subject who requires a reduction in the side-effects of a therapeutic agent. Furthermore, the terms include any subject who requires improved tolerability to any therapeutic agent for an adrenergic dysregulation therapy.

The pharmaceutically acceptable hydrophilic matrix as herein disclosed may comprise polysaccharides, for example, cellulose derivatives. Examples of such polysaccharides include alkylcelluloses, such as, methylcellulose; hydroxyalkylcelluloses, for example, hydroxymethylcellulose, hydroxyethylcellulose, hydroxypropylcellulose and hydroxybutylcellulose; hydroxyalkyl alkylcelluloses, such as, hydroxyethyl methylcellulose and hydroxypropyl methylcellulose; carboxyalkylcelluloses, such as, carboxymethylcellulose; alkali metal salts of carboxyalkylcelluloses, such as, sodium carboxymethylcellulose; carboxyalkylalkylcelluloses, such as, carboxymethylethylcellulose; carboxyalkylcellulose esters; other natural, semi-synthetic, or synthetic polysaccharides, such as, alginic acid, alkali metal and ammonium salts thereof. By way of example, the pharmaceutically acceptable hydrophilic matrix is a cellulose ether derivative. The cellulose ether derivative is a hydroxypropyl methylcellulose.

The hydrophilic matrix may include hydroxypropyl methyl cellulose (HPMC). Different viscosity grades of HPMC are commercially available. The HPMC may have a hydroxypropoxyl substitution of from about 7 to about 12 weight percent, a methoxyl substitution of from about 28 to about 30 weight percent, a number average molecular weight of about 86,000 and a 2% aqueous solution viscosity of about 4000 cps. The HPMC may have a hydroxypropoxyl substitution of from about 7 to about 12 weight percent, a methoxyl substitution of from about 19 to about 24 weight percent, a number average molecular weight of about 246,000 and a 2% aqueous solution viscosity of about 100,000 cps. Mixtures of the above HPMC's may be used. The hydrophilic matrix may comprise a hydroxypropyl methylcellulose such as Methocel®, which is manufactured by the Dow Chemical Company, U.S.A.

The hydrophilic matrix may also comprise polyacrylic acids and the salts thereof, crosslinked acrylic acid-based polymers, for example CARBOPOL™ polymers (Lubrizol Corp., Wickliffe, Ohio); polymethacrylic acids and the salts thereof, methacrylate copolymers; polyvinylalcohol; polyvinylpyrrolidone, copolymers of polyvinylpyrrolidone with vinyl acetate; combinations of polyvinylalcohol and polyvinylpyrrolidone; polyalkylene oxides such as polyethylene oxide and polypropylene oxide and copolymers of ethylene oxide and propylene oxide.

The HPMC may be admixed with additional hydrophilic polymers, for example, starch, pregelatinized starch, monosaccharides, or disaccharides. By way of example, the HPMC may be admixed with dextrose, sucrose, lactose, lactulose, trehalose, maltose, mannitol, sorbitol or combinations thereof. For example, the lactose or lactose monohydrate may be used. Different grades of lactose may be used. The lactose is a modified spray-dried lactose monohydrate (316 Fast Flow, WI). Other lactose monohydrates, may also be used. The particles of lactose monohydrate may be such that 98% (w/w) of the particles are smaller than 850 µm. The hydrophilic matrix may comprise a HPMC admixed with a partially gelatinized starch or a combination/admixture of lactose and partially gelatinized starch. By way of example, Starch 1500® NF (Colorcon, West Point, Pa.) which is described by the manufacturer as a partially gelatinized starch, may be used.

Extended release periods of the $\alpha_2$-adrenergic receptor agonist may be provided by manipulation of the hydrophilic matrix or manipulation of the hydrophilic matrix and a release retardant. By way of example, an eight hour release period for the $\alpha_2$-adrenergic receptor agonist may be provided using a hydrophilic matrix comprising Methocel® E4M which has a hydroxypropoxyl substitution of from about 7 to about 12 weight percent, a methoxyl substitution of from about 28 to about 30 weight percent, a number average molecular weight of about 86,000, a 2% aqueous solution of viscosity of about 4000 cps and 95% by weight may pass through a 100 mesh screen. By way of example, a twelve hour release period for the $\alpha_2$-adrenergic receptor agonist may be provided using a hydrophilic matrix comprising Methocel® K100M, which has a hydroxypropoxyl substitution of from about 7 to about 12 weight percent, a methoxyl substitution of from about 19 to about 24 weight percent, a number average molecular weight of about 246,000, a 2% aqueous solution of viscosity of about 100,000 cps and at least 90% by weight may pass through a 100 mesh screen. By way of example, up to a twenty four hour release period for the $\alpha_2$-adrenergic receptor agonist may be provided using a hydrophilic matrix comprising, for example, Methocel®, and a release retardant.

The formulation disclosed may also optionally comprise pharmaceutically acceptable formulating agents in order to promote the manufacture, compressibility, appearance and taste of the formulation. These formulating agents comprise, for example, diluents or fillers, glidants, binding agents, granulating agents, anti-caking agents, lubricants, flavors, dyes and preservatives. For example, the formulation may contain other pharmacologically-acceptable excipients for modifying or maintaining the pH, osmolarity, viscosity, clarity, color, sterility, stability, rate of dissolution, taste or odor of the formulation. The formulation may contain still other pharmacologically-acceptable excipients for modifying or maintaining the stability of one or more compounds of the composition. Such excipients are those substances usually and customarily employed to formulate dosages for administration in either unit dose or multi-dose form. The formulation herein described may be a solid oral dosage form. The solid oral dosage form is generally a tablet, capsule or gelcap. Among the optional formulating agents that further may be comprised in the matrix formulation may include, for example polyvidone; acacia gum; gelatin; alginic acid, sodium and calcium alginate; ethylcellulose; glidants such as colloidal silica, or talc; lubricants such as magnesium stearate and/or palmitate, calcium stearate, stearic acid, and polyethylene glycol.

The method can also include co-administering a therapeutically effective amount of a compound or formulation described herein and at least one other additional therapeutic agent. The composition may be co-formulated or administered with one or more additional therapeutic agents. Any therapeutic agent that is typically used in the treatment, prevention, and reduction of adrenergic dysregulation may also be administered or co-formulated with the formulations herein disclosed. The additional therapeutic agents may be administered within (either before or after) 14 days, 7 days, 24 hours, 12 hours, 1 hour, or simultaneously with the composition and/or formulations herein disclosed. Any suitable additional therapeutic agent may be co-formulated with the composition herein described or administered to the mammal being treated with this composition at concentrations known to be effective for these agents. The formulation with or without the additional agents may be administered orally or parenterally by injection, although other effective administration forms, such as intra-articular injection, intradermal injection, inhalant mists, transdermal iontophoresis or suppositories are also envisioned. The compounds and pharmaceutical formulations described herein may be used with other methods of treating and/or preventing ADHD. Other methods of treating and/or preventing ADHD include, for example, stimulants such as methylphenidate, Ritalin, Concerta, amphetamines, Adderall®, dextroamphetamines, Dexedrine®, modafinil, Provigil®, aminepine (Survector®); anti-depressants such as bupropion; nonstimulants such as Selective Norepinephrine Reuptake Inhibitors (SNRIs); tricyclic anti-depressants; Selective Serotonin Reuptake Enhancers (SSREs) such as tianeptine (Stablon®), bupropion (Wellbutrin®); and combinations thereof. The compounds and pharmaceutical formulations described herein may be used with known methods for treating hypertension, such as: ACE inhibitors such as captopril, enalapril, fosinopril (Monopril®), lisinopril (Zestril®), quinapril, ramipril (Altace®); angiotensin II receptor antagonists: e.g., irbesartan (Avapro®), losartan (Cozaar®), valsartan (Diovan®), candesartan (Atacand®); alpha blockers such as doxazocin, prazosin, or terazosin; beta blockers such as atenolol, labetalol, metoprolol (Lopressor®, Toprol-XL®); calcium channel blockers such as amlodipine (Norvasc®), diltiazem, verapamil; diuretics, such as bendroflumethiazide, chlortalidone, hydrochlorothiazide; and combinations thereof.

Methods of diagnosing and monitoring the presence or change of adrenergic dysregulation condition are generally known. To assess whether the formulations disclosed herein are useful to treat, reduce, or prevent an adrenergic dysregulation condition, any method known in the art may be used. For example, a medically desirable result for an ADHD or hypertension condition may be a reduction of impulsiveness or blood pressure, respectively. ADHD or hypertension may be diagnosed and/or monitored, for example, by physical examination of the subject before, during and after administration of the herein disclosed formulations.

The following examples describe embodiments of the invention. It will be appreciated that the amount of the agonist and its ratio with the components of the hydrophilic matrix and release-retardant with or without additional agents required for use in the treatment or prevention of an adrenergic dysregulation condition and its related complications will vary within wide limits and may be adjusted to the individual requirements of a particular subject. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements (e.g., weights).

EXAMPLES

The following examples are not intended to be limiting.

Example 1

Tablet Preparation

A preblend was prepared as follows: API (clonidine HCl, USP; Spectrum Chemical, New Brunswick, N.J.); hydroxypropyl methylcellulose (Hypromellose, USP; Methocel® K100M Premium, Dow Chemical), lactose monohydrate NF 316 Fast Flow® (Formost Farms, WI) pre-screened through 20 mesh was used (Tablets 1 and 2), the lactose carrier, were mixed in a V-blender, and then collected.

The pre-blend from above was combined with pre-screened partially pregelatinized starch, NF (Starch 1500®; Colorcon, PA); sodium lauryl sulfate (Spectrum Chemical, NJ) and colloidal silicon dioxide (Cab-0-Sil® M-5P; Cabot, Mass.) into a 2 qt. V-blender; and mixed for about 8 minutes; followed by a charge of pre-screened magnesium stearate and further mixing for 3 minutes. The powder was pelletized using a Fette 1200i Tablet Press to provide Tablet 1. The lactose carrier may be added before or after dry compaction of the powdered blend depending on the particular kind and particle size of the lactose. In a similar manner, additional Tablets 2-4 were prepared, and their compositions are summarized in Table 1. Tablet 5 was also prepared and its composition is summarized in Table 1.

The tablets may be film coated with art-known film coating compositions. The coating may be applied to improve the aspect and/or the taste of the tablets and the ease with which they may be swallowed. Coating the tablets may improve stability and shelf-life. Suitable coating formulations comprise a film-forming polymer such as, for example, hydroxypropyl methylcellulose, e.g. hypromellose 2910, a plasticizer such as, for example, a glycol, e.g. propylene glycol or polyethylene glycol, an opacifies, such as, for example, titanium dioxide, and a film smoothener, such as, for example, talc. Suitable coating solvents are water as well as organic solvents. Examples of organic solvents are alcohols, e.g. ethanol or isopropanol, ketones, e.g. acetone, or halogenated hydrocarbons, e.g. methylene chloride. Optionally, the coating may contain a therapeutically effective amount of one or more API's to provide for an immediate release of the API(s) and thus for an immediate relief of the symptoms treated by the API(s). An ethylcellulose coating, such as Surelease® (Colorcon, PA) may be applied to the tablets in a pan coater or a fluidized bed coater.

TABLE 1

|  | wt % of Formula | Wgt. (mg)/ Tablet |
|---|---|---|
| Pre-blend |  |  |
| Clonidine HCl, USP | 0.1% |  |
| Lactose Monohydrate, NF (316 Fast Flow ®, modified spray-dried) | 44.1% |  |
| HPMC, USP (Methocel ® K100M Premium CR, Dow) | 55.8% |  |
| TOTAL | 100.0% |  |
| Tablet 1 | | |
| Clonidine HCl, USP | 0.07% | 0.1 |
| Lactose Monohydrate, NF (316 Fast Flow ®, modified spray-dried) | 64.0% | 96.0 |
| HPMC, USP (Methocel ® K100M Premium CR, Dow) | 35.0% | 52.5 |
| Colloidal Silicon Dioxide, NF (Cab-O-Sil ® M-5P) | 0.2% | 0.3 |
| Magnesium Stearate, NF | 0.73% | 1.1 |
| TOTAL | 100.0% | 150.0 |
| Tablet 2 | | |
| Pre-blend | 68.1% | 81.7 |
| Partially Pregelatinized Starch, NF (Starch 1500 ®) | 30.7% | 36.9 |
| Colloidal Silicon Dioxide, NF (Cab-O-Sil ® M-5P) | 0.20% | 0.2 |
| Magnesium Stearate, NF | 1.0% | 1.2 |
| TOTAL | 100.0% | 120.0 |
| Tablet 3 | | |
| Pre-blend | 68.1% | 81.7 |
| Partially Pregelatinized Starch, NF (Starch 1500 ®) | 25.7% | 30.9 |
| Sodium lauryl sulfate (SLS) | 5.0% | 6.0 |
| Colloidal Silicon Dioxide, NF (Cab-O-Sil ® M-5P) | 0.2% | 0.2 |
| Magnesium Stearate, NF | 1.0% | 1.2 |
| TOTAL | 100.0% | 120.0 |
| Tablet 4 | | |
| Clonidine HCl, USP | 0.08% | 0.1 |
| Sodium lauryl sulfate (SLS) | 1.7% | 2.0 |
| Lactose Monohydrate, NF (316 Fast Flow ®, modified spray-dried) | 30.0% | 36.0 |
| HPMC, Type 2208, USP (Methocel ® K100M Premium CR) | 38.0% | 45.6 |

TABLE 1-continued

|  | wt % of Formula | Wgt. (mg)/ Tablet |
|---|---|---|
| Partially Pregelatinized Starch, NF (Starch 1500 ®) | 29.1% | 34.9 |
| Colloidal Silicon Dioxide, NF (Cab-O-Sil ® M-5P) | 0.2% | 0.2 |
| Magnesium Stearate, NF | 1.0% | 1.2 |
| TOTAL | 100.0% | 120.0 |
| Tablet 5 | | |
| Clonidine HCl, USP (SIMS) | 0.333% | 0.4 |
| Sodium Lauryl Sulfate (SLS), NF (Spectrum) | 5.933% | 7.00 |
| Lactose Monohydrate, NF (316 Fast Flow ®, modified spray-dried) | 27.500% | 33.00 |
| Hypromellose, Type 2208, USP (Methocel ® K100M DC Grade) | 38.000% | 45.60 |
| Partially Pregelatinized Starch, NF (Starch 1500 ®) | 27.383 | 32.86 |
| Colloidal Silicon Dioxide, NF (Cab-O-Sil ® M-5P) | 0.200% | 0.24 |
| Magnesium Stearate, NF | 0.750% | 0.90 |
| TOTAL | 100.00% | 120.00 |

Example 2

Active Release Profile

Figure 1B:
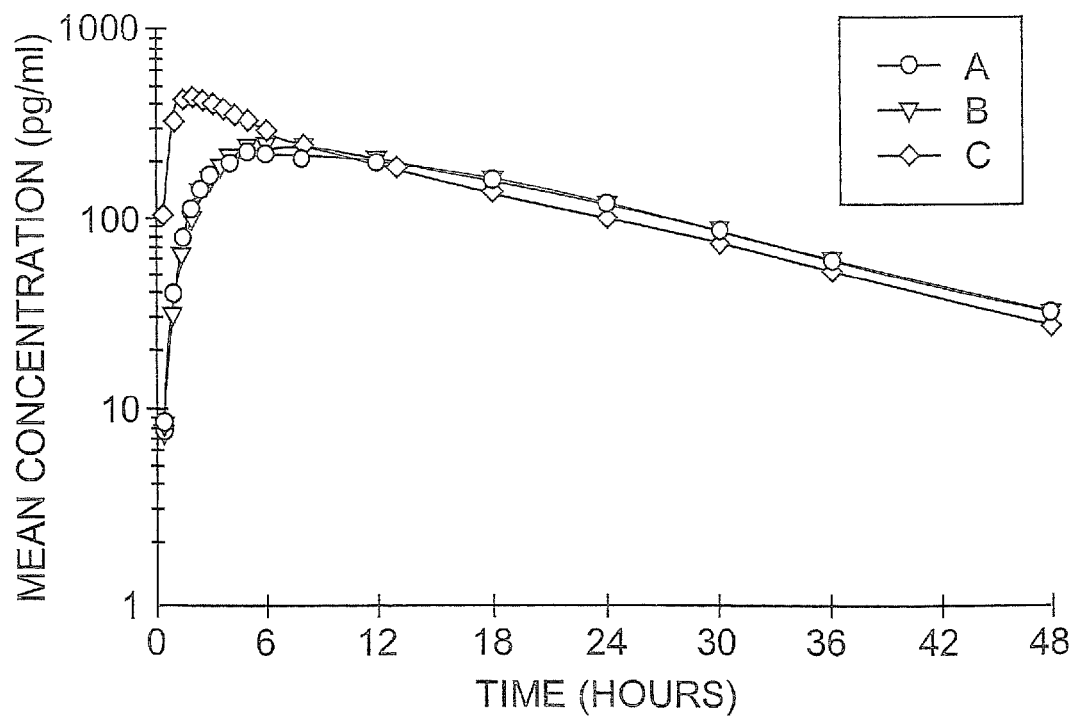
Figure 2:
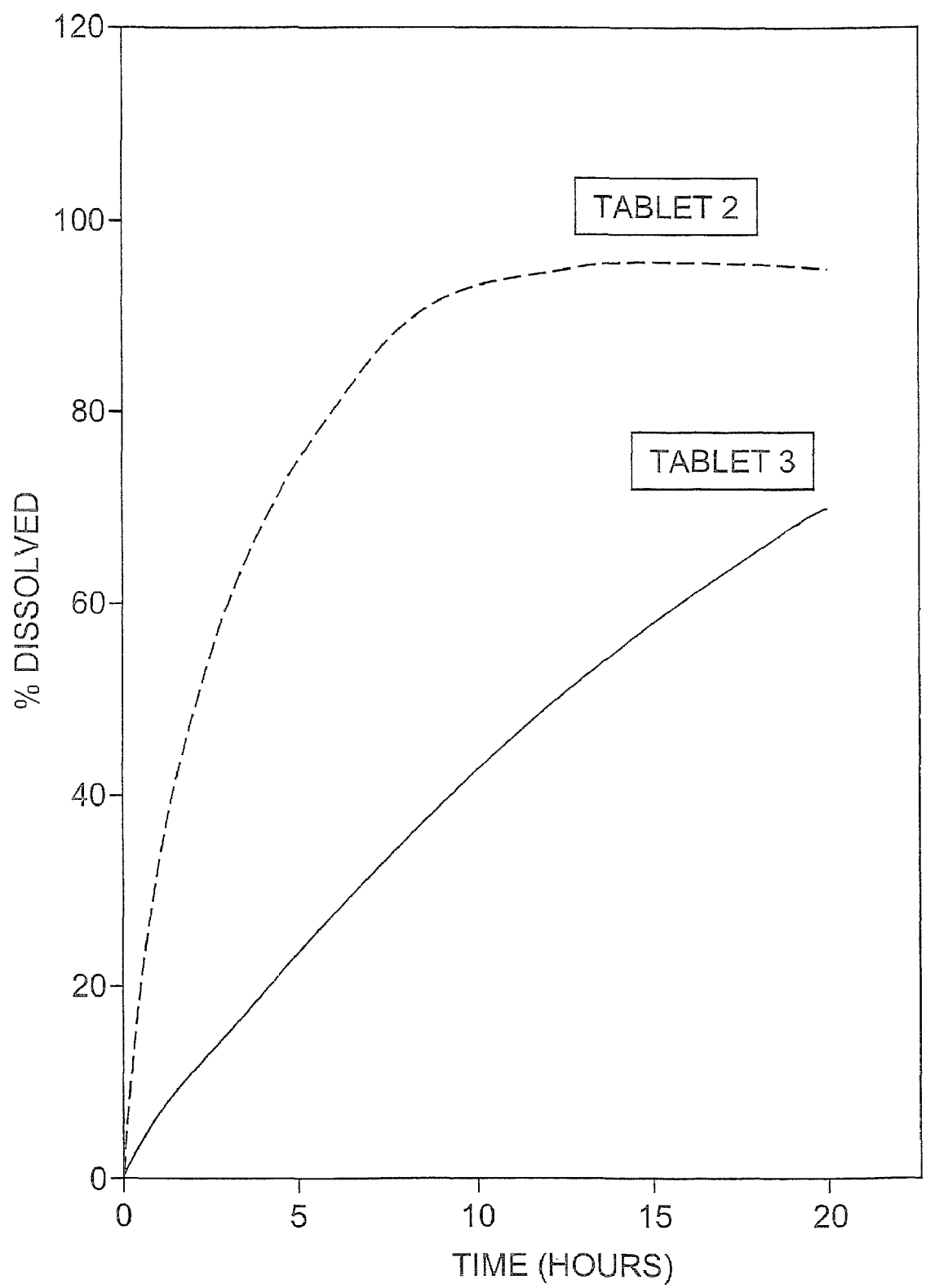
FIG. 2 is a graphical representation of predicted area under the curve (AUC) blood plasma levels of an exemplary extended release composition embodiment disclosed herein in comparison with an immediate release composition.

Experimental results of the dissolution of clonidine from the Tablets 2 and 3 using the USP paddle method (500 mL, 50 RPM) in a pH 2 medium are depicted in FIG. 1. The release profile is expressed as the % clonidine dissolved from the medium as a function of time. The extended release profiles of clonidine from the hydrophilic matrix with and without release-retardant are shown graphically. As shown in FIG. 1, Tablet 3, with release retardant provides a zero- to first-order release profile of clonidine as compared to Tablet 2, which is absent the release-retardant.

Example 3

Clinical Study of Single Dose Pharmacokinetics

During each of three treatment periods, subjects received one of the following treatments in a randomized order: Clonicel (clonidine HCl sustained release) 0.1 mg while fasting, Clonicel 0.1 mg following a standardized meal and Catapres (clonidine HCl immediate release) 0.1 mg while fasting. Blood samples for the measurement of plasma clonidine were collected pre-dose and for 48 hours following dosing. A minimum washout period of seven days separated dose administrations. A total of 15 healthy study subjects, male and female, were enrolled in the study.

After the administration of Clonicel, maximum clonidine concentrations are lower and occur at later times relative to clonidine concentrations after the administration of Catapres. In the present study, the $C_{max}$, after administration of Clonicel-fasted was approximately 50% of Catapres $C_{max}$, values (235±34.7 pg/mL vs. 443±59.6 pg/mL). The mean time to reach maximum concentration ($T_{max}$) as also longer, 6.80 hours, for Clonicel-fasted when compared to Catapres, which was 2.07 hours. Mean estimates of the apparent half-life of clonidine after the administration of Clonicel-fasted and Catapres are similar, 12.67 hours and 12.52 hours, respectively. For comparisons using an ANOVA model, the 90% confidence interval for comparing the maximum exposure of clonidine, based on $\ln(C_{max})$, after Clonicel-fasted vs. Catapres is not within 80% to 125% limits. However, the 90% confidence intervals for comparing total systemic exposure, based on $\ln(AUC_{last})$ and $\ln(AUC_{inf})$, are within the 80% to 125% limits, indicating the total systemic exposure to clonidine is similar after the administration of Clonicel-fasted and Catapres. Clonidine plasma concentration-time profiles are similar after the administration of Clonicel under fasted and fed conditions. In the present study, Tmax values were 6.80 hours (fasted) and 6.50 hours (fed) and clonidine concentrations were comparable for administration under each condition. Food had no effect on the elimination half-life of Clonicel (12.67 hours-fasted vs. −12.65 hours-fed). The clonidine $C_{max}$, $AUC_{last}$, and $AUC_{inf}$ ratios (fed vs. fasted) are within the 90% confidence intervals of 80% to 125%, indicating that food does not have a significant effect on either the rate or extent of absorption of clonidine from the Clonicel formulation. Overall, the plasma-concentration time profile of Clonicel was delayed and more sustained when compared to Catapres under fasted conditions and was unaffected by the presence of food. Data are shown in Tables 2, 3 and 4.

Example 4

Clinical Study of Steady-State Plasma Concentrations

A 4-week (28 days), multi-center, double-blind, randomized, parallel group study of the steady-state pharmacokinetics and pharmacodynamics of three oral dosing regimens of Clonicel: 0.2, 0.4, and 0.6 mg/day was conducted. The doses in this study were chosen based on the recommended usual oral daily dose range for clonidine prescribed for hypertension and the expectation that the chosen doses would provide the range of plasma clonidine concentrations associated with efficacy in the treatment of hypertension (0.2 to 2.0 ng/mL). All doses were administered on a divided dose schedule, i.e., 0.1, 0.2, and 0.3 mg b.i.d., with 12 hours separating the doses. A total of 40 patients were projected for enrollment to achieve a minimum of 36 evaluable patients (12 per treatment arm) randomly assigned to one of the three treatment groups. Prior to random assignment to treatment, patients underwent a 2-week washout period of current antihypertensive medications. For the treatment period, an escalating titration schedule was implemented to achieve the assigned target dose.

TABLE 2

Pharmacokinetic Parameters of Clonidine

| Parameter | Treatment A: CLONICEL-Fasted | | | | Treatment B: CLONICEL-Fed | | | | Treatment C: CATAPRES-Fasted | | | |
|---|---|---|---|---|---|---|---|---|---|---|---|---|
| | n | Mean | SD | CV % | n | Mean | SD | CV % | n | Mean | SD | CV % |
| $T_{max}$ (hr) | 15 | 6.80 | 3.61 | 53.05 | 14 | 6.50 | 1.23 | 18.88 | 15 | 2.07 | 0.50 | 23.96 |
| $C_{max}$ (pg/mL) | 15 | 235 | 34.7 | 14.76 | 14 | 258 | 33.3 | 12.89 | 15 | 443 | 59.6 | 13.45 |
| $AUC_{last}$ (hr*pg/mL) | 15 | 5790 | 1167 | 20.16 | 14 | 5985 | 1112 | 18.57 | 15 | 6698 | 1415 | 21.12 |
| $AUC_{inf}$ (hr*pg/mL) | 15 | 6505 | 1728 | 26.56 | 14 | 6729 | 1650 | 24.52 | 15 | 7313 | 1812 | 24.78 |
| $AUC_{Extrap}$ (%) | 15 | 9.95 | 5.88 | 59.09 | 14 | 9.98 | 5.75 | 57.61 | 15 | 7.66 | 4.62 | 60.35 |
| $\lambda_x$ (hr$^{-1}$) | 15 | 0.0585 | 0.0142 | 24.23 | 14 | 0.0579 | 0.0126 | 21.76 | 15 | 0.0584 | 0.0134 | 22.95 |
| $T_{1/2}$ (hr) | 15 | 12.67 | 3.76 | 29.66 | 14 | 12.65 | 3.56 | 28.12 | 15 | 12.52 | 3.11 | 24.83 |
| $T_{last}$ (hr) | 15 | 48.01 | 0.03 | 0.06 | 14 | 47.16 | 3.21 | 6.81 | 15 | 48.00 | 0.00 | 0.00 |
| $C_{last}$ (pg/mL) | 15 | 34.6 | 19.2 | 55.48 | 14 | 36.3 | 18.6 | 51.30 | 15 | 30.6 | 18.3 | 59.69 |

TABLE 3

Statistical Analysis of the Log-transformed Systemic Exposure Parameters of Clonicel-fasted (Treatment A) vs. Catapres-fasted (Treatment C).

| Dependent Variable | Geometric Mean$^a$ | | Ratio (%)$^b$ | 90% CI$^c$ | | ANOVA | |
|---|---|---|---|---|---|---|---|
| | Test | Ref | (Test/Ref) | Lower | Upper | Power | CV % |
| ln ($C_{max}$) | 232.6308 | 439.5037 | 52.93 | 50.26 | 55.74 | 1.0000 | 7.96 |
| ln ($AUC_{last}$) | 5690.0446 | 6573.2536 | 86.56 | 81.51 | 91.93 | 0.9998 | 9.26 |
| ln ($AUC_{inf}$) | 6332.2870 | 7126.9267 | 88.85 | 83.04 | 95.06 | 0.9993 | 10.42 |

TABLE 4

Statistical Analysis of the Log-transformed Systemic Exposure Parameters of Clonicel-fed (Treatment B) vs. Catapres-fasted (Treatment A).

| Dependent Variable | Geometric Mean$^a$ | | Ratio (%)$^b$ | 90% CI$^c$ | | ANOVA | |
|---|---|---|---|---|---|---|---|
| | Test | Ref | (Test/Ref) | Lower | Upper | Power | CV % |
| ln ($C_{max}$) | 255.3212 | 232.5085 | 109.81 | 104.21 | 115.71 | 0.9999 | 7.68 |
| ln ($AUC_{last}$) | 5846.4142 | 5677.2826 | 102.98 | 96.13 | 110.32 | 0.9990 | 10.11 |
| ln ($AUC_{inf}$) | 6495.4962 | 6322.5606 | 102.74 | 94.14 | 112.12 | 0.9912 | 12.86 |

Ambulatory blood pressure monitoring (ABPM), using an appropriate monitor, was performed at Baseline prior to dosing and on the last day of dosing (Day 26). Ten blood samples to measure steady-state plasma concentrations of clonidine were collected pre-dose and for a 12-hour period following the morning dose on each of Days 23 and 25. Patients were discontinued from study medication immediately after completion of the 26-day dosing period, although they were sequestered for 48 hours (Days 27 and 28) for blood pressure and safety assessments. All patients were domiciled in the research unit specifically during all study periods that required procurement of ABPM data and blood samples for PK analyses. There were 39 patients in the PK/PD Population (12 each in the 0.2 mg/day and the 0.4 mg/day groups; and 15 in the 0.6 mg/day group), and 42 patients in the Safety Population (12 in the 0.2 mg/day group; 15 each in the 0.4 mg/day and the 0.6 mg/day groups). The active was formulated into round, white, Clonicel 0.1 mg oral sustained release tablets containing 0.1 mg clonidine hydrochloride.

Figure 11:
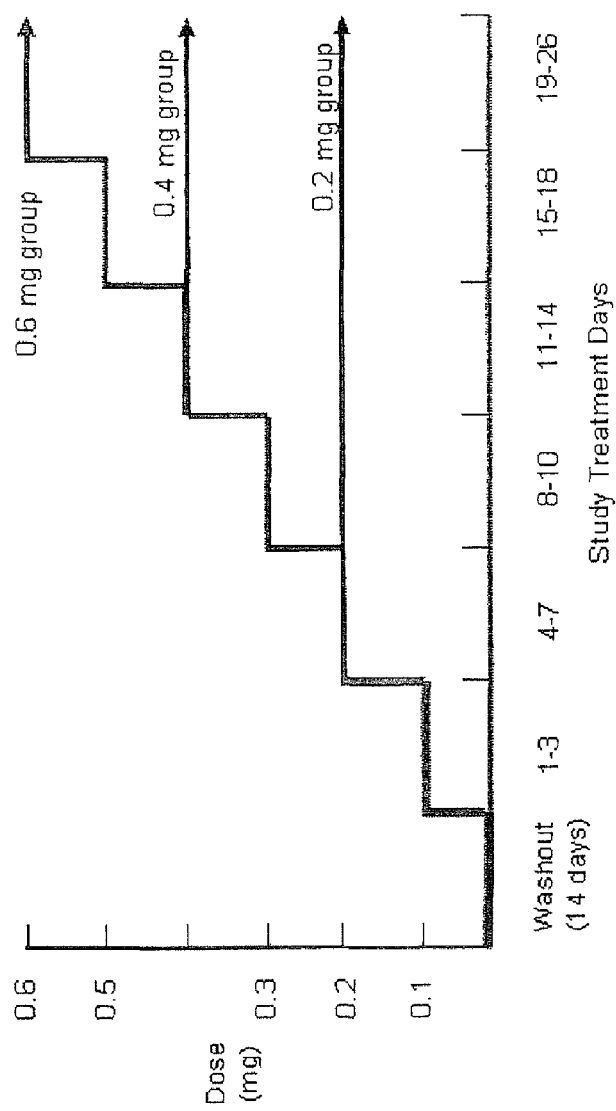
FIG. 11 depicts the escalating titration schedule used to reach steady-state plasma concentrations of clonidine.

To reach steady-state plasma concentrations of the active, an escalating titration schedule was implemented. The schedule is shown in FIG. 11.

Blood samples at pre-specified intervals pre- and post study drug treatment were obtained on Days 23 and 25 for correlation of pharmacokinetics with results of ABPM obtained on Day 26-28 of the study.

Pharmacokinetic parameters for clonidine were calculated using noncompartmental analysis. Reported parameters, as defined herein, included: Maximum plasma concentrations of clonidine, observed by inspection of individual subject plots of plasma concentration versus time ($C_{max}$); Time (h) from dosing to $C_{max}$ observed by inspection of individual subject plots of plasma concentration versus time ($T_{max}$); Minimum plasma concentrations of clonidine, observed by inspection of individual subject plots of plasma concentration versus time ($C_{min}$); The average concentration during a dosing interval at steady-state. Calculated as ($AUC_{0-\tau}/\tau(C_{avg})$; the fluctuation ratio for steady-state data=$C_{max}/C_{min}$; The areas under the plasma concentration-time curve during the 12-hour dosing interval at steady-state, calculated using the linear trapezoidal method ($AUC\tau$); and The apparent oral clearance at steady-state calculated as the dose administered divided by $AUC\tau(CL/Fss)$. Individual patient pharmacokinetic analyses were conducted using actual blood sampling times and the times of dose administration. Concentration-time data that were below the limit of quantification (BLQ) were treated as zero (0.00 pg/mL) for calculation of descriptive statistics. In the pharmacokinetic analysis, BLQ concentrations were treated as zero from time-zero up to the time at which the first quantifiable concentration was observed; embedded and/or terminal BLQ concentrations were treated as "missing". Non-compartmental pharmacokinetic parameters were calculated from plasma concentrations of clonidine on Days 23 and 25 using WinNonlin® version 5.2 (Pharsight Corp). Since Clonicel was administered at fixed doses, independent of body weight or size, CL/F values were normalized to body weight on a per kg basis. All derived pharmacokinetic parameters and plasma concentrations at each scheduled assessment time point were summarized with descriptive statistics (mean, standard error of the mean, standard deviation, coefficient of variation, median, range and number of observations). Graphical displays of individual subject and mean (for a given dosage level) plasma concentration versus time data were also generated.

Initial assessment of pharmacodynamic data (ABPM measurements) evaluated the effects of Clonicel in producing decreases in mean systolic and diastolic blood pressures across all three treatment groups. Mean baseline ABPM data for the three treatment groups were compared with mean data obtained on Day 26 (last day of treatment) and on Days 27 and 28. A more detailed PK/PD analysis was conducted by using the individual patient ABPM data to compare the blood pressure profile at Baseline and on Day 26 of treatment. The daytime (0- to 12-hour) intervals were used in the analysis, since pharmacokinetic data were collected on Day 25, over the daytime 12-hour dosing interval at steady state. In order to investigate the maintenance of effect at the tail end of the inter-dosing interval, differences between the SBP, DBP, and HR values at Baseline and the last two hours in the inter-dosing interval (Hours 11 and 12) on Day 26 were calculated for each patient. Paired t-tests were performed to test the significance of these differences between Baseline and the last two measuring times. The approach taken to quantify the effects of clonidine on blood pressure was to calculate the difference between the areas under the BP vs. time curves ($AUC_{BP}$) at Baseline and on Day 26. These values were used to relate the pharmacodynamic effect to dose, as well as to conduct the PK/PD analyses. Relationships between the pharmacodynamic effects and pharmacokinetic parameters including $AUC\tau$, $C_{max}$, and $C_{min}$, were evaluated using the sigmoidal $E_{max}$, model as follows: $E=(E_{max} \cdot C^{\gamma})/(C^{\gamma}+EC_{50}^{\gamma})$, where E is the observed magnitude of the pharmacological effect at a given concentration; C or AUC is the drug concentration or AUC producing the pharmacological effect; $E_{max}$ is the estimated, maximal pharmacological effect; $EC_{50}$ is the concentration at which the effect is 50% of the maximal effect; $EC_{90}$ is the concentration at which the effect is 90% of the maximal effect; and $\gamma$ is the Shape factor (steepness of slope) for the E vs. C relationship.

Analysis of Pharmacokinetic Data

Figure 3:
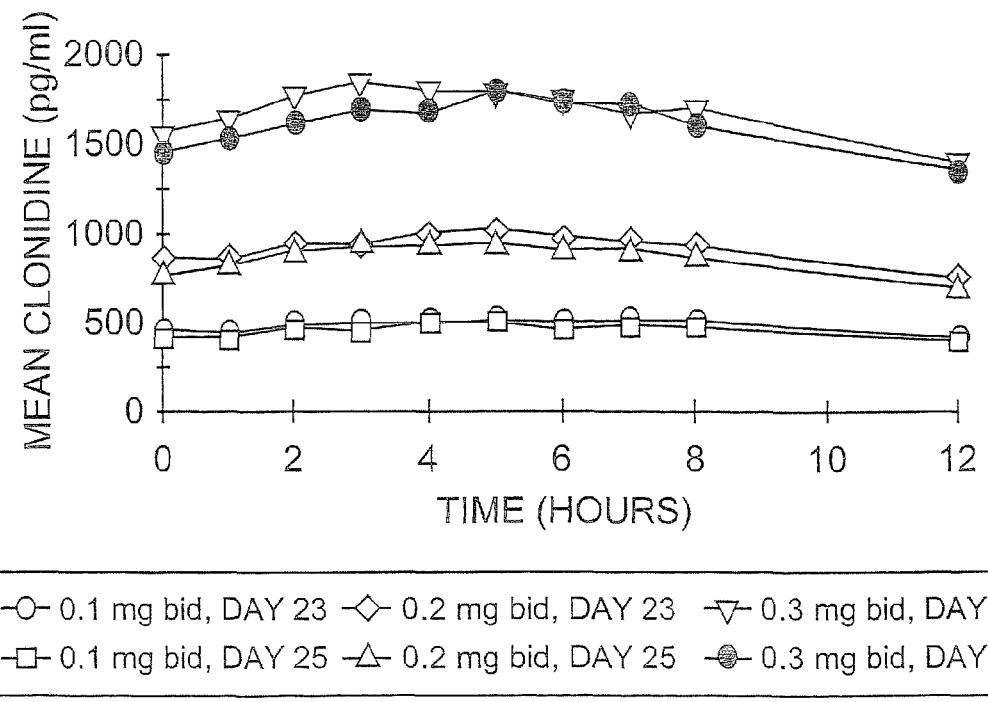
FIG. 3 depicts the mean clonidine concentration-time profiles by treatment group for days 23 and 25. Average concentrations for the 3 treatment groups ranged from approximately 400 pg/mL to 1800 pg/mL. Plasma concentrations increased proportionately with increase in dose, stayed fairly even throughout the inter-dosing interval, and were very similar between Days 23 and 25.
Figure 4:
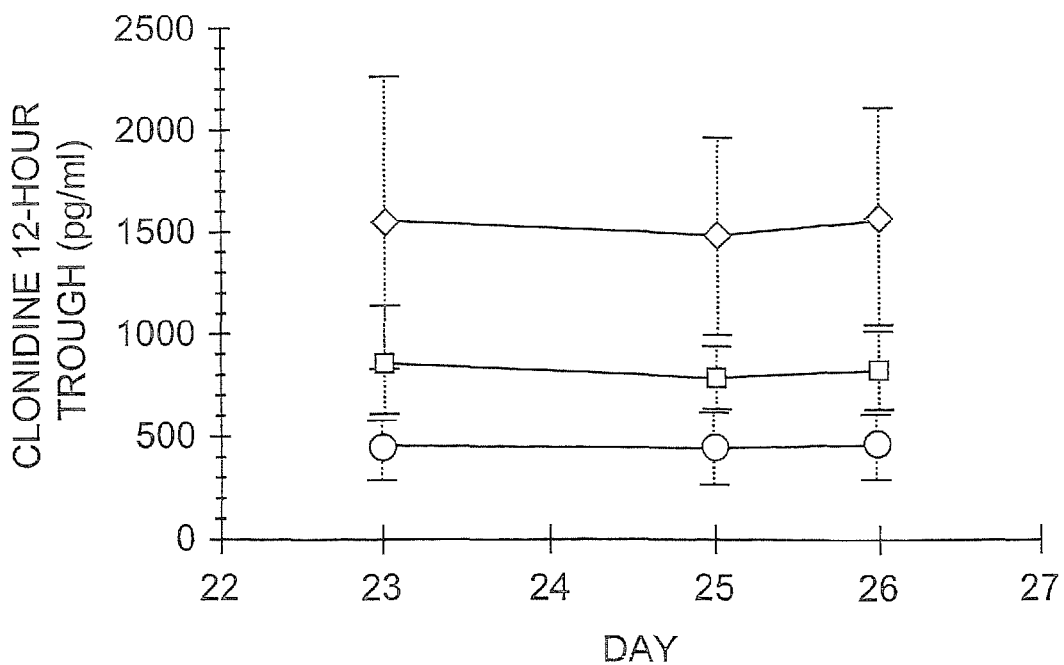
FIG. 4 depicts the mean (±SD) steady-state trough clonidine concentrations on days 23, 25 and 26. The relationship between dose and derived PK parameters was explored by plotting $C_{max}$, $C_{min}$, $AUC_t$, and CL/F values for Day 25 as a function of the administered dose. As the figure shows, the three exposure parameters appeared to increase proportionately with the dose, and CL/F decreased slightly over the dosing range.

A total of 21 blood samples were collected from each patient at steady state for the assay of clonidine plasma concentrations, 10 samples on Day 23, 10 samples on Day 25, and 1 sample on Day 26. Plasma concentrations are tabulated individually by patient and plotted in FIG. 3. Average concentrations for the 3 treatment groups ranged from approximately 400 pg/mL to 1800 pg/mL. The figure shows that plasma concentrations increased proportionately with increase in dose, stayed fairly even throughout the inter-dosing interval, and were very similar between Days 23 and 25. Achievement of steady-state was confirmed by summarizing and plotting mean trough concentrations prior to the morning doses of Days 23, 25, and 26. Summary data are plotted in FIG. 4. As the figure shows, plasma clonidine concentrations were at steady-state beginning on Day 23 and throughout the sampling period. Three independent, repeated-measures ANOVA tests were performed, one for each group, to verify that the trough levels on Days 23, 25, and 26 were not statistically different. The F values and corresponding p-values for the 0.2, 0.4, and 0.6 mg groups were: $F(2.22)=2.3$, $p=0.1237$; $F(2.20)=1.277$, $p=0.3008$; $F(2.28)=17.15$, $p=0.53$, respectively. None of the ANOVA tests reached statistical significance, confirming the lack of difference between the 3 time points and the achievement of steady state.

Plasma concentrations at trough were also used to calculate intra-subject variability. It was important to investigate intra-subject variability in plasma concentration as an index of the consistency of pharmacokinetic performance between individual dosing units. The mean intra-subject coefficients of variation were very low and ranged from 10% to 12% for the three groups, thus indicating that the sustained-release formulation delivered clonidine consistently from day to day.

Steady-state noncompartmental pharmacokinetic parameters were calculated for each patient individually and summarized across treatment groups for Days 23 and 25. Table 5 shows the key parameters by treatment group and Day of treatment. Average $C_{max}$ values ranged from 553 pg/mL for the 0.2 mg group at Day 23 to 1980 pg/mL for the 0.6 mg group at Day 23. The same pattern was evident for $C_{min}$ and $AUC_\tau$. $T_{max}$ averaged 4 to 5 hours at all dose levels, with an overall range for individual patients from 2 to 8 hours, although the majority (>60%) of the observed $T_{max}$ values occurred between 4 and 6 hours. For the main derived PK parameters, the coefficients of variation (CVs) ranged from 18% to 42% with higher CVs observed at the highest dose, indicating a low inter-subject variability in pharmacokinetic exposure. Overall, there were no major differences in mean values between Days 23 and 25. The sustained-release property of the CLONICEL® formulation at steady-state was evident from the low $C_{max}/C_{min}$ mean ratios observed for the three treatment groups. These mean ratios averaged 1.4 to 1.5 indicating a low peak to trough fluctuation. The relationship between dose and derived PK parameters was explored by plotting $C_{max}$, $C_{min}$, $AUC_\tau$ and CL/F values for Day 25 as a function of the administered dose in FIG. 4. As the figure shows, the three exposure parameters appeared to increase proportionately with the dose, and CL/F decreased slightly over the dosing range.

Analyses of Pharmacodynamic Data

Figure 6A:
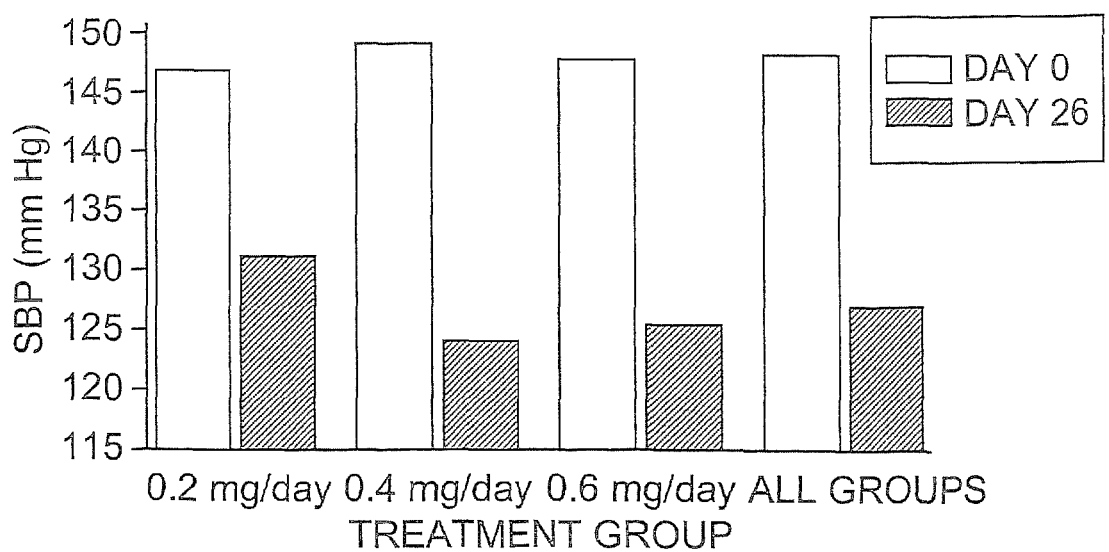
FIGS. 6A, 6B and 6C depict the mean daytime SBP (systolic blood pressure), DBP (diastolic blood pressure), and change from Baseline to day 26.
Figure 6B:
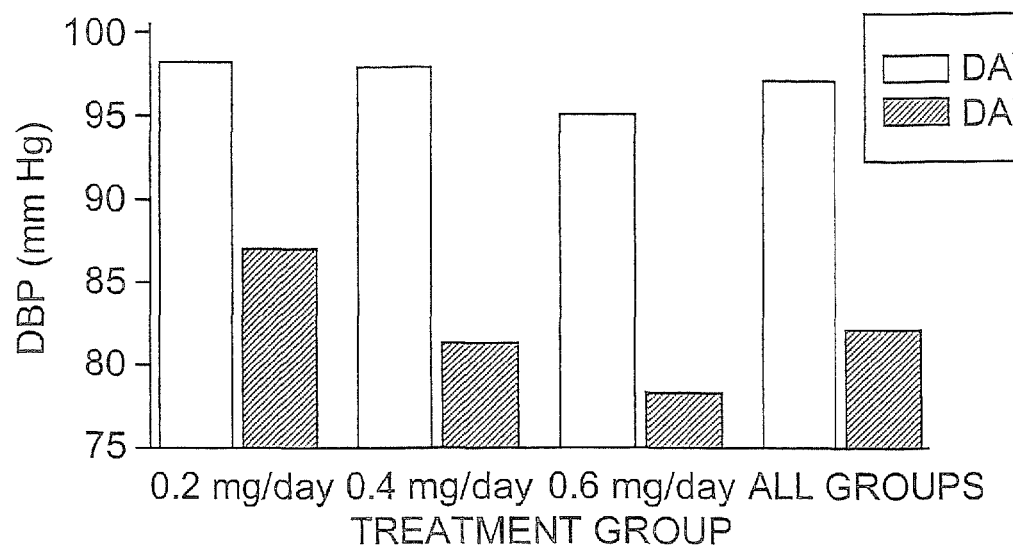
Figure 6C:
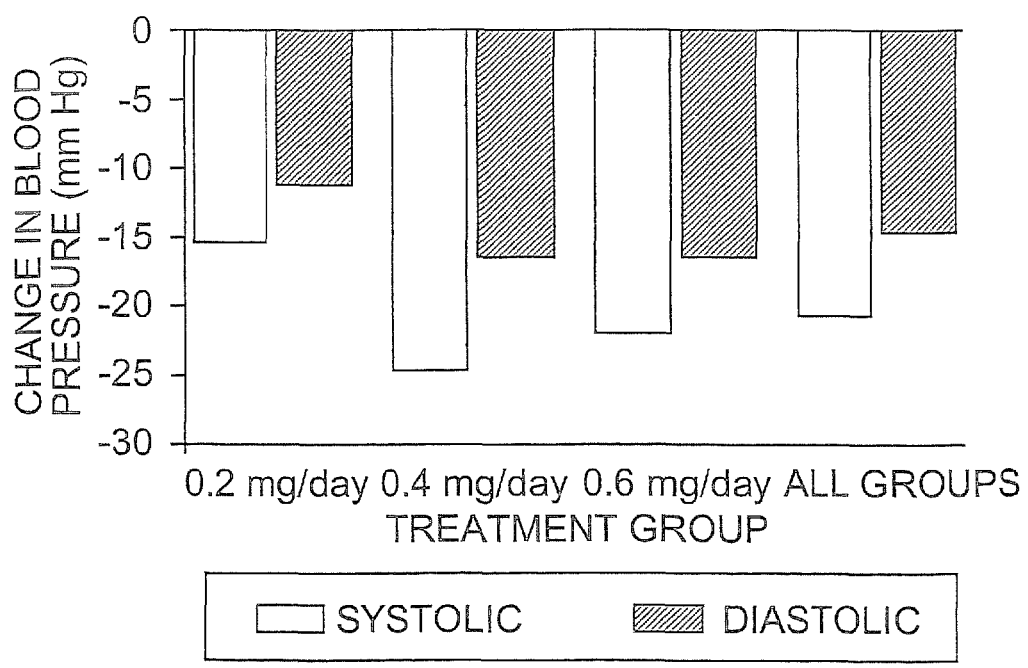

Administration of Clonicel® at all three doses produced meaningful changes in daytime, nighttime and composite 24-hour systolic and diastolic blood pressures. The difference between Baseline and Day 26, the last day of treatment, was considered of primary importance from a pharmacodynamic perspective. Table 6 summarizes the mean daytime systolic and diastolic blood pressure observations on Baseline (Day 0) and on Days 26, 27 and 28; and FIG. 6 summarizes the data on Days 0 and 26. There was a dose-dependent reduction in mean daytime systolic and diastolic blood pressures (relative to baseline) at the 0.2 mg/day to 0.4 mg/day dose levels (15.5 mmHg and 25 mmHg reduction in mean SBP, respectively, and 11.2 mmHg and 16.6 mmHg reduction in mean DBP, respectively). However, the high dose of 0.6 mg/day did not produce further decrease in blood pressure (23.3 mmHg and 16.9 mmHg reduction in mean daytime SBP and DBP, respectively), indicating a possible plateau in blood pressure control beyond 0.4 mg/day. Forty-eight hours after abrupt cessation of study dosing, both systolic and diastolic blood pressures returned very closely to their baseline values with-

TABLE 5

| Treatment Group | | | $C_{max}$ (pg/mL) | $T_{max}$ (h) | $C_{min}$ (pg/mL) | $C_{max}/C_{min}$ Ratio | AUCτ (h*pg/mL) |
|---|---|---|---|---|---|---|---|
| | | | | Parameter | | | |
| 0.2 mg | Day | Mean | 553 | 5.00 | 407 | 1.38 | 5867 |
| (n = 12) | 23 | SD | 157 | 2.09 | 138 | 0.14 | 1735 |
| | Day | Mean | 560 | 4.25 | 375 | 1.52 | 5627 |
| | 25 | SD | 183 | 1.65 | 119 | 0.26 | 1594 |
| 0.4 mg | Day | Mean | 1060 | 4.42 | 762 | 1.42 | 11050 |
| (n = 12) | 23 | SD | 291 | 1.16 | 241 | 0.12 | 3196 |
| | Day | Mean | 986 | 4.67 | 709 | 1.4 | 10410 |
| | 25 | SD | 173 | 1.15 | 147 | 0.14 | 2007 |
| 0.6 mg | Day | Mean | 1980 | 4.47 | 1380 | 1.44 | 20130 |
| (n = 15) | 23 | SD | 839 | 1.81 | 568 | 0.12 | 8207 |
| | Day | Mean | 1870 | 5.02 | 1320 | 1.43 | 19310 |
| | 25 | SD | 636 | 1.52 | 451 | 0.18 | 6561 | out overshoot. The effect on blood pressure was maintained over the entire 12-hour daytime dosing interval at all doses, albeit lesser in magnitude for the 0.2 mg/day dose and between 10 and 12 hours after dosing.

TABLE 6

| Treatment Group (mg/day) | SBP (mmHg) | | | | DBP (mmHg) | | | |
|---|---|---|---|---|---|---|---|---|
| | Day 0 | Day 26 | Day 27 | Day 28 | Day 0 | Day 26 | Day 27 | Day 28 |
| 0.2 (n = 12) | 146.7 | 131.2 | 135.7 | 142.9 | 98.3 | 87.1 | 89.1 | 95.6 |
| 0.4 (n = 12) | 149.1 | 124.1 | 130.0 | 143.9 | 97.9 | 81.3 | 84.3 | 94.7 |
| 0.6 (n = 15) | 147.5 | 124.2 | 134.0 | 150.4 | 95.0 | 78.1 | 83.7 | 95.5 |
| Groups Combined (n = 39) | 147.7 | 126.7 | 133.3 | 146.1 | 97.0 | 81.9 | 85.5 | 95.3 |

Figure 7A:
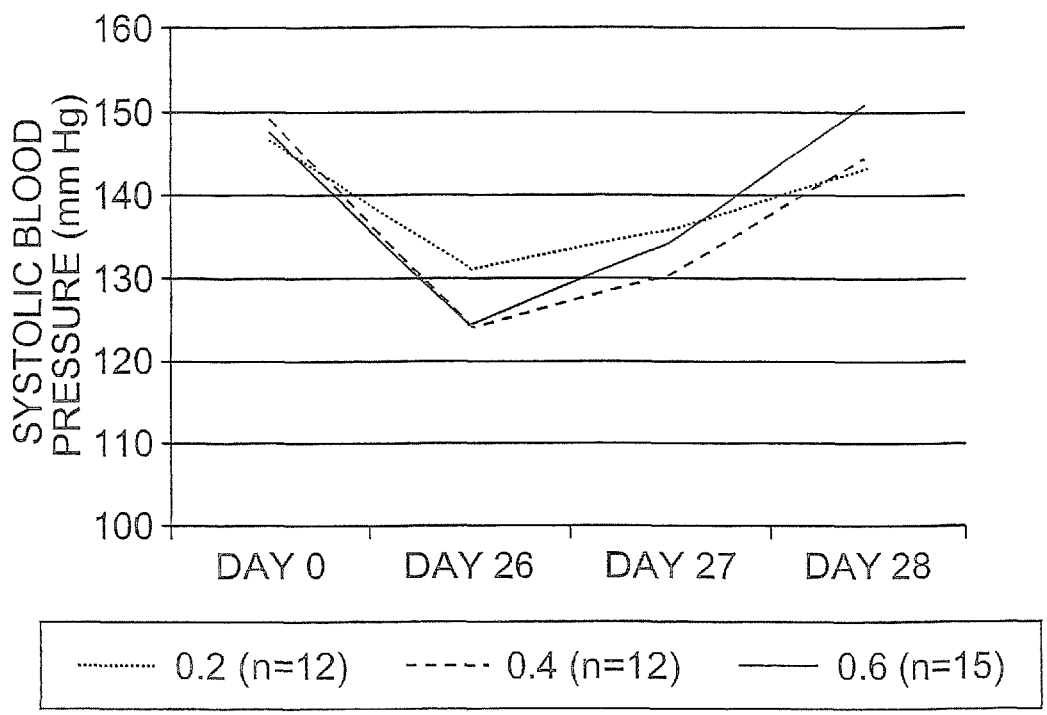
FIGS. 7A and 7B depict the mean daytime systolic and diastolic blood pressure observations at Baseline and for Days 26 to 28. As is evident from the data, both SBP and DBP daytime values gradually returned to Baseline levels over the 48 hours post-dosing without overshoot even though study medication had been withdrawn abruptly.
Figure 7B:
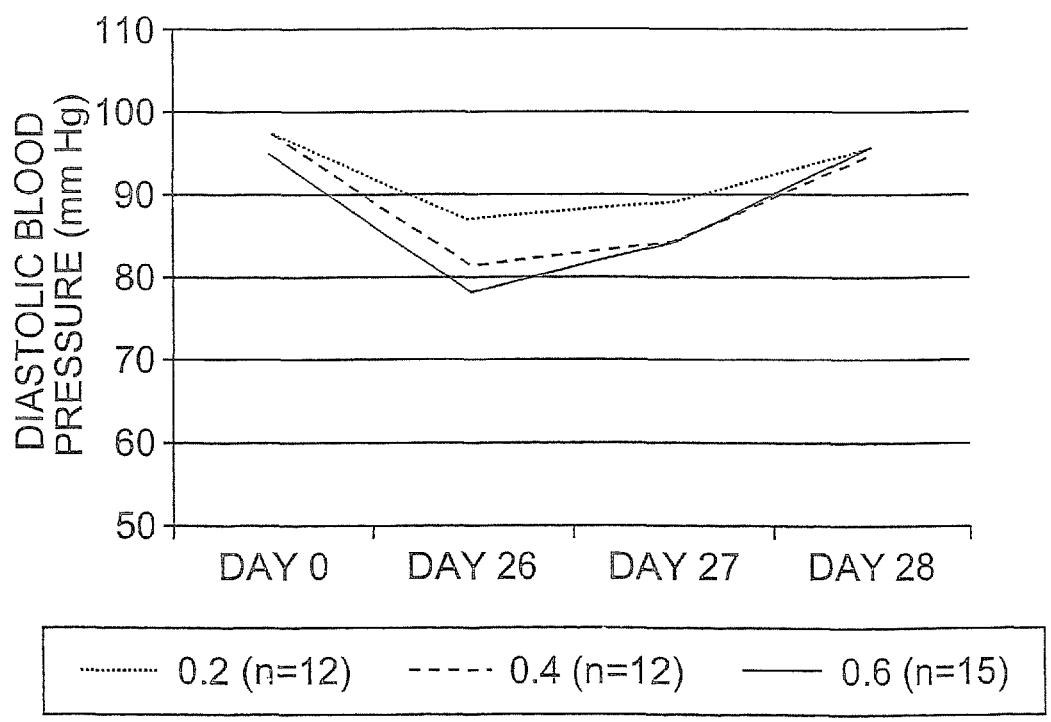

To investigate potential rebound hypertension following abrupt discontinuation of treatment with Clonicel, study drug was discontinued without tapering after the PM dose on Day 26. ABPM assessments were continued for 48 hours following this last dose. Table 6 and FIG. 7 summarize the mean daytime systolic and diastolic blood pressure observations at Baseline and for Days 26 to 28. As is evident from the data, both SBP and DBP daytime values gradually returned to Baseline levels over the 48 hours post-dosing without overshoot even though study medication had been withdrawn abruptly.

Figure 8A:
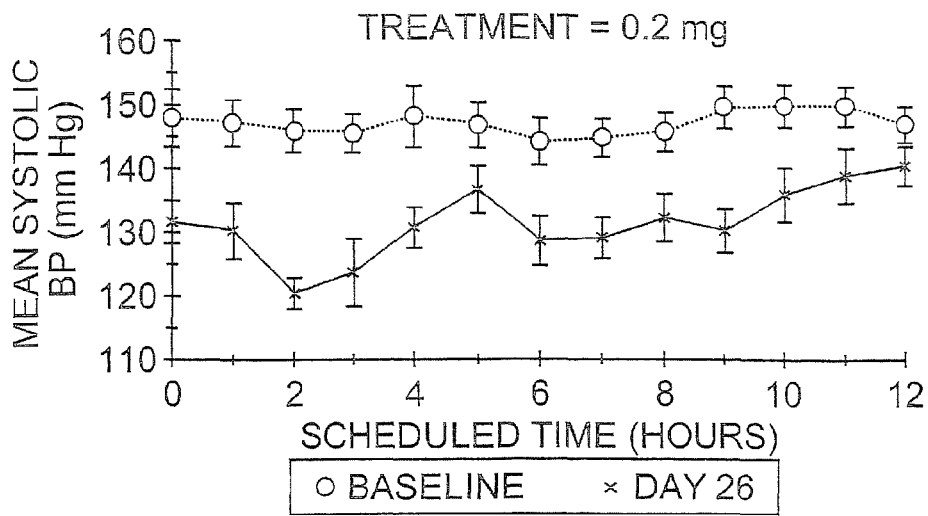
FIGS. 8A, 8b and 8C depict the mean SBP profiles by treatment at baseline and day 26.
Figure 8B:
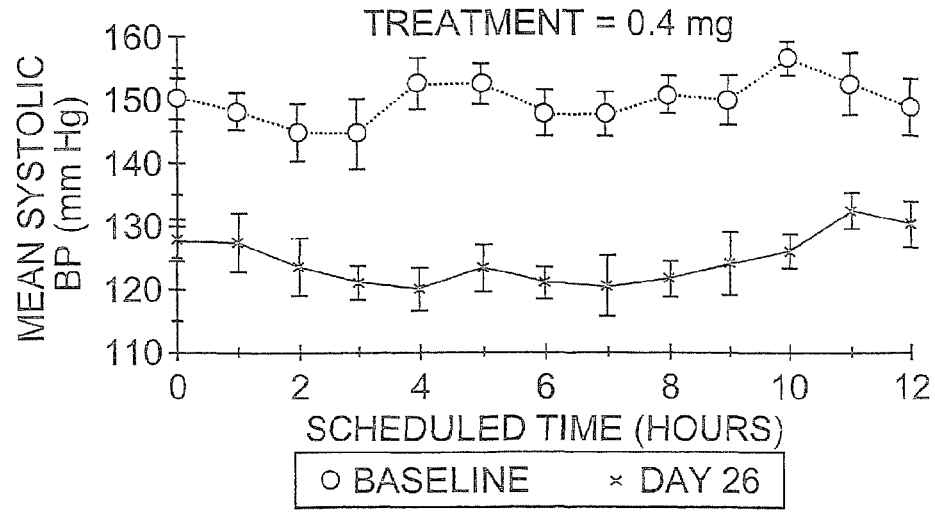
Figure 8C:
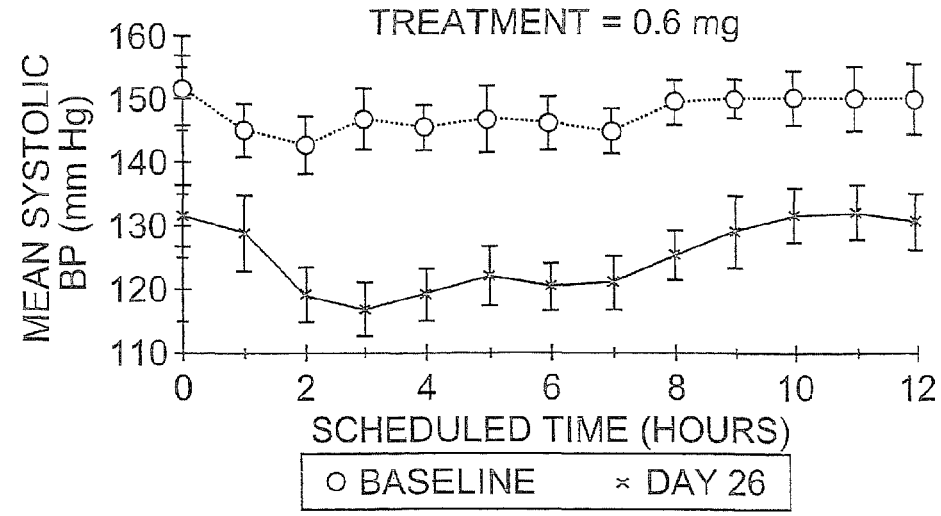
Figure 9A:
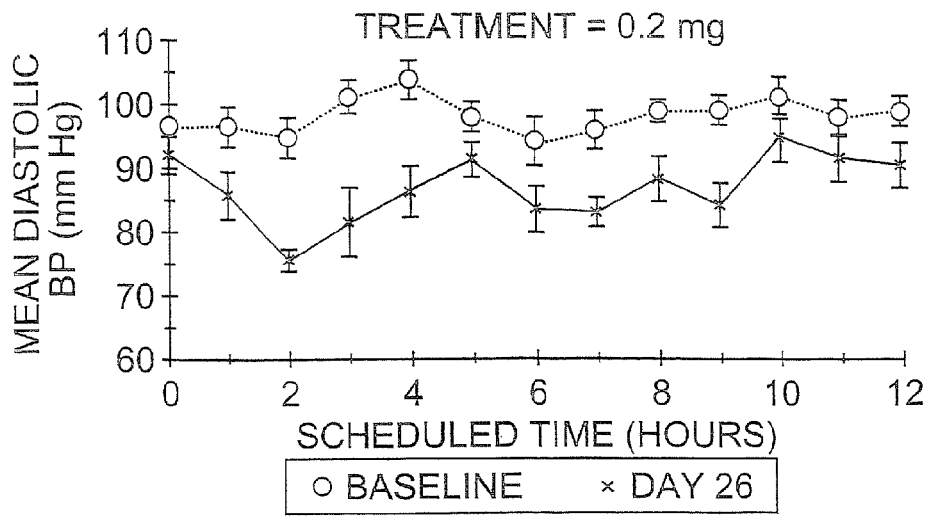
FIGS. 9A, 9B and 9C depict the mean DBP profiles by treatment at baseline and day 26.
Figure 9B:
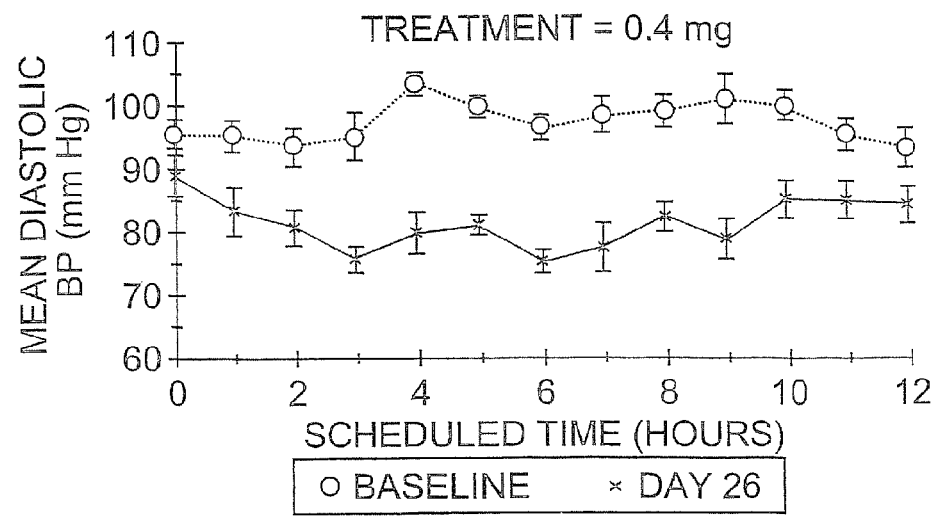
Figure 9C:
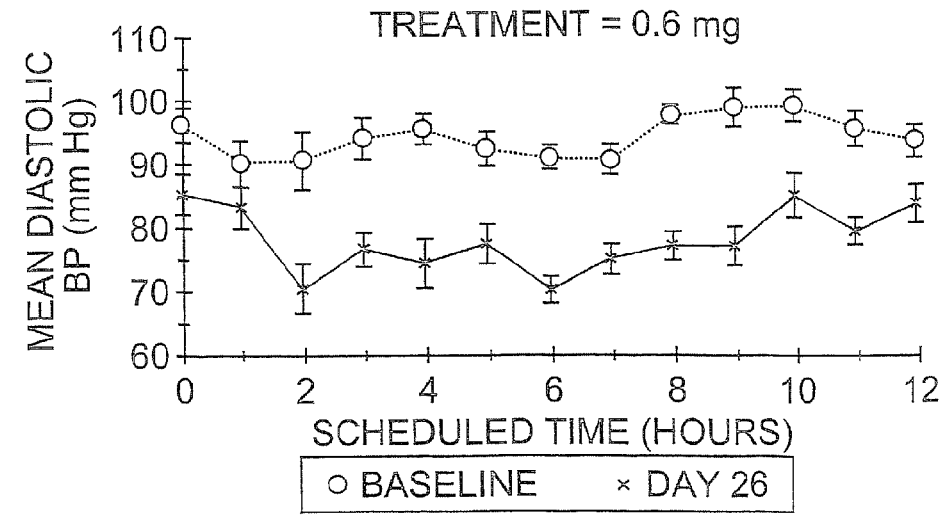
Figure 10A:
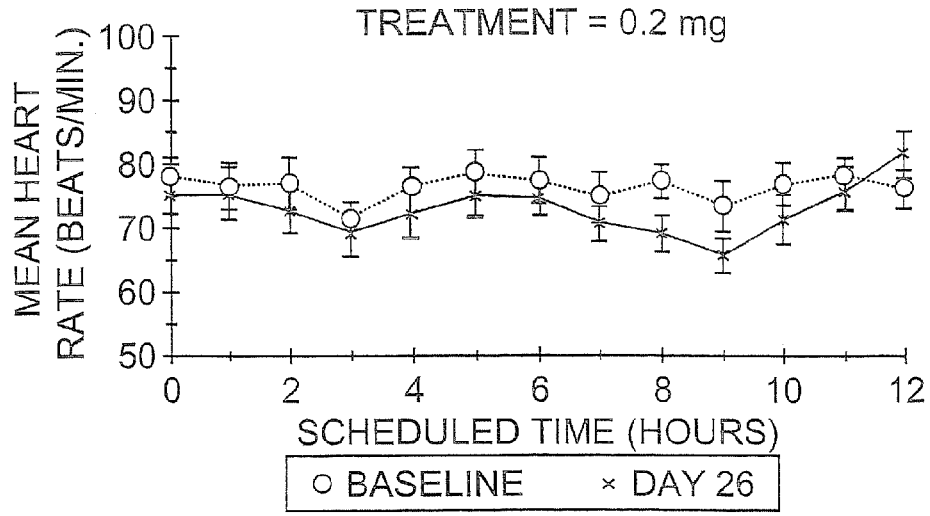
FIGS. 10A, 10B and 10C depict the mean heart rate profiles by treatment at baseline and day 26.
Figure 10B:
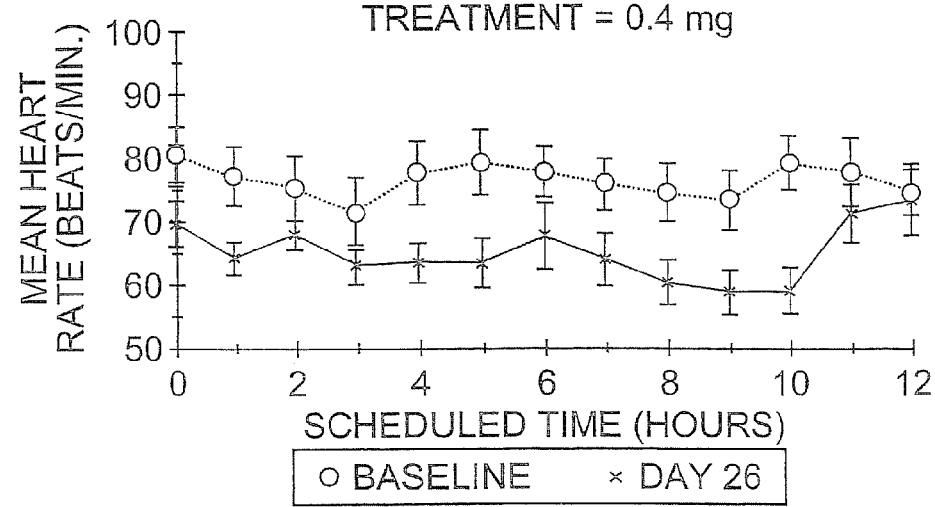
Figure 10C:
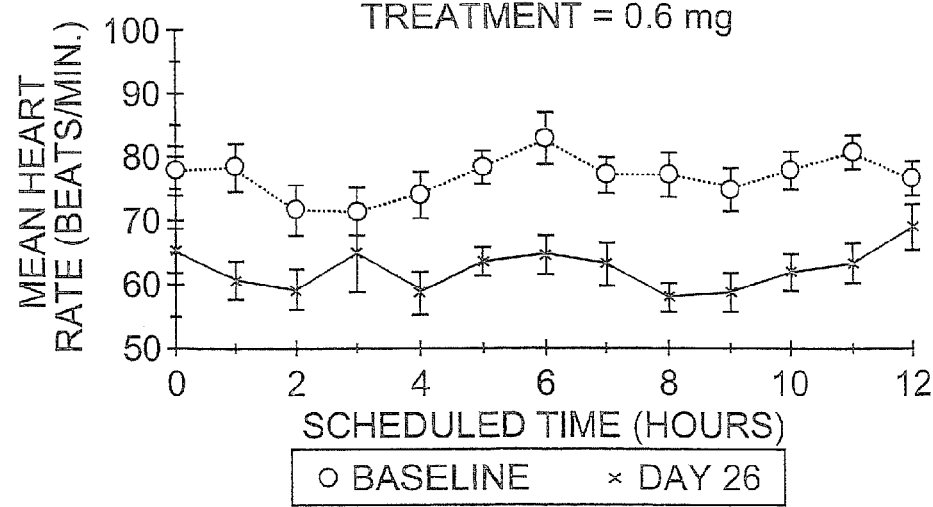

The pharmacodynamic effects of Clonicel throughout the inter-dosing interval were investigated by summarizing and plotting ABPM data between the morning and evening doses on Day 26, the last day of dosing. For comparison, ABPM data collected at Baseline between the same time points were also summarized and plotted. Decreases in blood pressure were observed for all but two patients during Clonicel treatment: the hypotensive effects were negligible for in one patient (0.2 mg/day treatment group) and absent in another (0.6 mg/day treatment group). Mean pharmacodynamic effect versus time data are plotted in FIGS. 8, 9 and 10. As observed in previous summaries, the magnitude of the effect of the morning dose on blood pressure in the 0.2 mg group appeared to be less than that elicited by the higher doses. Similar effects on blood pressure and heart rate were observed in the inter-dosing interval for the 0.4 and 0.6 mg groups. The duration of the effect on blood pressure was maintained over the entire 12-hour daytime dosing interval at the higher doses, albeit lesser in magnitude between 10 and 12 hours after dosing. To investigate the maintenance of effect at the tail end of the inter-dosing interval, differences between the SBP, DBP, and HR values at Baseline and the last two hours in the inter-dosing interval (Hours 11 and 12) on Day 26 were calculated for each patient. Table 7 summarizes the mean differences by treatment group and presents paired t-tests of the significance of these differences between Baseline and the last two measuring times. As the table shows, consistent statistically significant differences were maintained at the last 2 measuring times for SBP and DBP at the higher two dosing groups, but were more intermittent for the 0.2 mg/day group. With the exception of the difference between Hour 11 and Baseline at the 0.6 mg group, there were no statistically significant differences for HR at the last two measuring times.

TABLE 7

| Parameter | Treatment Group | Hour 11 mean-diff (mm Hg) | p-value | Hour 12 mean-diff (mm Hg) | p-value |
|---|---|---|---|---|---|
| Systolic Blood Pressure | 0.2 mg | 10.82 | 0.0308 | 6.50 | 0.0676 |
|  | 0.4 mg | 21.91 | 0.0023 | 18.25 | 0.0021 |
|  | 0.6 mg | 19.57 | 0.0053 | 19.33 | 0.0044 |
| Diastolic Blood Pressure | 0.2 mg | 6.273 | 0.1037 | 8.500 | 0.0120 |
|  | 0.4 mg | 10.64 | 0.0052 | 9.000 | 0.0070 |
|  | 0.6 mg | 17.00 | 0.0003 | 19.33 | 0.0044 |
| Heart Rate | 0.2 mg | 2.545 | 0.4468 | −5.333 | 0.0762 |
|  | 0.4 mg | 7.727 | 0.1052 | 12.50 | 0.7731 |
|  | 0.6 mg | 18.14 | 0.0029 | 7.667 | 0.1392 |

Pharmacokinetic-Pharmacodynamic Relationships

Figure 5:
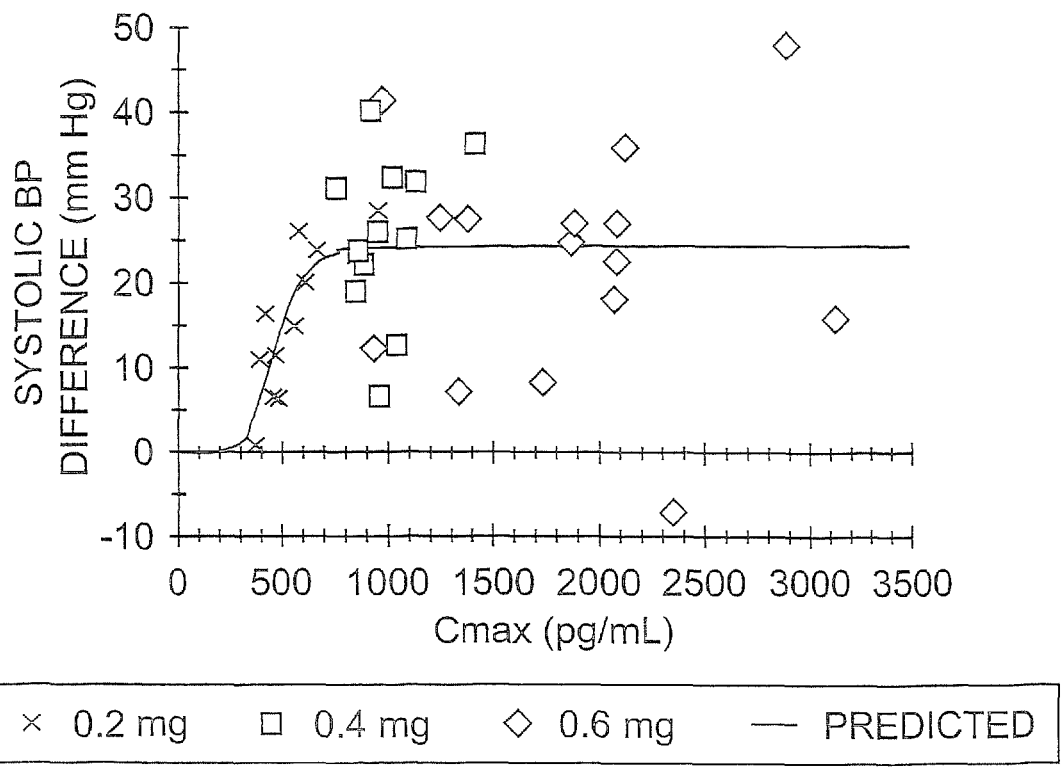
FIG. 5 depicts a sigmoidal $E_{max}$ relationship between effect on systolic blood pressure and clonidine $C_{max}$.

Pharmacokinetic-pharmacodynamic modeling was conducted using the blood pressure response data and the $C_{max}$, $C_{min}$ and $AUC\tau$ values at Day 25 of dosing. The sigmoidal $E_{max}$ model (WinNonlin PD Model 105) was used with the assumption that there is no pharmacological effect at zero drug concentration. The relationships between effect and exposure were similar for changes in diastolic and systolic blood pressure for each of the 3 exposure parameters. A representative plot of the observed data, identified by Clonicel dose level, with the superimposed curve fit is displayed in FIG. 5. In general, the sigmoidal $E_{max}$ model described well the relationship between blood pressure effects and clonidine concentration. The slope of the concentration-response ($\gamma$) is quite steep at the low concentrations provided by administration of the 0.2 mg daily dose of Clonicel. Parameter estimates for the model fits for the effects on blood pressure are summarized in Table 8. These results indicate that the clonidine concentration required to produce 50% of the maximal response on systolic blood pressure is 458 pg/mL for $C_{max}$ and 359 pg/mL for $C_{min}$. Concentrations of this magnitude were consistently achieved in the 0.4 and 0.6 mg groups, but not in the 0.2 mg group. The estimated $EC_{90}$ for clonidine effects on systolic blood pressure indicated that $C_{max}$ and $C_{min}$ concentrations of 646 and 532 pg/mL, respectively, are required. All of the patients in the 0.4 and 0.6 mg groups achieved >500 pg/mL clonidine concentrations, but based on the relationship between effect and concentration, it is apparent that little additional benefit accrues from the increase in dose beyond 0.4 mg/day. The data in Table 8 summarize the PK/PD parameters from the sigmoidal $E_{max}$ model.

TABLE 8

| Parameter |  | Systolic BP | Diastolic BP |
|---|---|---|---|
| $C_{max}$ | $E_{max}$ ($\Delta$BP) | 24.3 | 16.7 |
|  | $EC_{50}$ (pg/mL) | 458 | 431 |
|  | $EC_{90}$ (pg/mL) | 646 | 561 |
|  | Shape Factor ($\gamma$) | 6.39 | 8.29 |
| $C_{min}$ | $E_{max}$ ($\Delta$BP) | 24.4 | 16.8 |
|  | $EC_{50}$ (pg/mL) | 359 | 341 |
|  | $EC_{90}$ (pg/mL) | 532 | 461 |
|  | Shape Factor ($\gamma$) | 5.56 | 7.31 |
| $AUC\tau$ | $E_{max}$ ($\Delta$BP) | 24.3 | 16.8 |
|  | $EC_{50}$ (pg/mL) | 4702 | 4401 |
|  | $EC_{90}$ (pg/mL) | 6692 | 5921 |
|  | Shape Factor ($\gamma$) | 6.26 | 7.42 |

A sustained release profile for the Clonicel formulation of clonidine was confirmed by a delayed $T_{max}$, a dampened $C_{max}$, prolonged concentrations of clonidine over the 12-hour dosing interval, and low fluctuation of the plasma clonidine concentrations over the dosing interval. The low fluctuation corresponds to the narrow peak-to-trough range provided by the sustained release formulation. Low intra-subject variability in the clonidine plasma concentration-time profiles was established over two 12-hour dosing intervals at steady-state, indicates consistent delivery of clonidine by the formulation. Significant decreases in blood pressure were observed at all dose levels during treatment, with dose-related decreases at 0.2 and 0.4 mg/day but with no clinically significant additional benefit at 0.6 mg/day. Effects were maintained over the entire 12 hours in the inter-dosing interval, especially for the 0.4 and 0.6 mg/day doses. PK/PD modeling indicates that blood pressure lowering and heart rate effects were related to the steady-state $AUC\tau$, $C_{max}$, and $C_{min}$ clonidine concentrations, with optimal effects observed at the 0.4 mg/day dose level.

Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims.

What is claimed is:

1. An oral dosage form comprising:
   (a) clonidine or a pharmaceutically acceptable salt thereof in an amount between about 0.001 wt % and 0.5 wt % of said oral dosage form; and
   (b) a pharmaceutically acceptable hydrophilic matrix comprising:
      (i) at least one hydroxypropyl methylcellulose ether in an amount between 20 wt % and 80 wt % of said oral dosage form;
      (ii) at least one of starch, lactose, or dextrose in an amount between 20 wt % and 80 wt % of said oral dosage form; and
      (iii) sodium lauryl sulfate in an amount of about 5 wt % of said oral dosage form;

wherein after administration of said dosage form no more than once about every 24 hours to a subject having a steady state plasma concentration of clonidine, the clonidine plasma concentration peak-to-trough ratio is no greater than about 1.9.

2. The oral dosage form of claim 1, wherein said clonidine or a pharmaceutically acceptable salt thereof is clonidine hydrochloride.

3. The oral dosage form of claim 1, wherein said amount of clonidine is between about 0.01 wt % to about 0.3 wt % of said oral dosage form.

4. The oral dosage form of claim 1, wherein said amount of clonidine or a pharmaceutically acceptable salt thereof is between about 0.025 mg to about 0.4 mg.

5. An oral dosage form comprising:
   (a) clonidine or a pharmaceutically acceptable salt thereof in an amount between about 0.001 wt % and 0.5 wt % of the oral dosage form;
   (b) a pharmaceutically acceptable hydrophilic matrix comprising,
      (i) at least one hydroxypropyl methylcellulose ether in an amount between 20 wt % and 80 wt % of the oral dosage form;
      (ii) at least one of starch, lactose, or dextrose in an amount between 20 wt % and 80 wt % of the oral dosage form; and
      (iii) sodium lauryl sulfate in an amount of about 5 wt % of said oral dosage form; and
   (c) a metal stearate and/or colloidal silica;

wherein after administration of said dosage form no more than once about every 24 hours to a subject having a steady state plasma concentration of clonidine, the clonidine plasma concentration peak-to-trough ratio is no greater than about 1.9.

6. The oral dosage form of claim 5, wherein said clonidine or a pharmaceutically acceptable salt thereof is clonidine hydrochloride.

7. The oral dosage form of claim 5, wherein the amount of clonidine is between about 0.01 wt % to about 0.3 wt % of the oral dosage form.

8. The oral dosage form of claim 5, wherein said amount of clonidine or a pharmaceutically acceptable salt thereof is between about 0.025 mg to about 0.4 mg.

9. The oral dosage form of claim 5, comprising:
   (a) clonidine hydrochloride in an amount between about 0.001 wt % and 0.5 wt % of the oral dosage form;
   (b) a pharmaceutically acceptable hydrophilic matrix comprising,
      (i) at least one hydroxypropyl methylcellulose ether in an amount between 30 wt % and 50 wt % of the oral dosage form;
      (ii) at least one of starch, lactose, or dextrose in an amount between 50 wt % and 70 wt % of the oral dosage form; and
      (iii) sodium lauryl sulfate in an amount of about 5 wt % of said oral dosage form; and
   (c) a metal stearate and/or colloidal silica.

10. An oral dosage form consisting essentially of:
    (a) clonidine hydrochloride in an amount between about 0.001 wt % and 0.5 wt % of the oral dosage form;
    (b) a pharmaceutically acceptable hydrophilic matrix comprising,
       (i) at least one hydroxypropyl methylcellulose ether in an amount between 30 wt % and 50 wt % of the oral dosage form;
       (ii) at least one of starch, lactose, or dextrose in an amount between 50 wt % and 70 wt % of the oral dosage form; and
       (iii) sodium lauryl sulfate in an amount of about 5 wt % of said oral dosage form; and
    (c) a metal stearate and/or colloidal silica;

wherein after administration of said dosage form no more than once about every 24 hours to a subject having a steady state plasma concentration of clonidine, the clonidine plasma concentration peak-to-trough ratio is no greater than about 1.9.

* * * * *